US009006403B2

(12) United States Patent
Liou et al.

(10) Patent No.: US 9,006,403 B2
(45) Date of Patent: Apr. 14, 2015

(54) PROCESSES FOR THE PREPARATION OF SGLT2 INHIBITORS

(75) Inventors: Jason Liou, San Diego, CA (US); Yuelin Wu, Pudong District (CN); Shengbin Li, Pudong District (CN); Ge Xu, Pudong New District (CN)

(73) Assignee: Theracos, Inc., Marlborough, MA (US)

( * ) Notice: Subject to any disclaimer, the term of this patent is extended or adjusted under 35 U.S.C. 154(b) by 359 days.

(21) Appl. No.: 13/600,985

(22) Filed: Aug. 31, 2012

(65) Prior Publication Data

US 2013/0046088 A1    Feb. 21, 2013

Related U.S. Application Data

(63) Continuation of application No. 12/545,400, filed on Aug. 21, 2009, now Pat. No. 8,283,454.

(60) Provisional application No. 61/091,248, filed on Aug. 22, 2008.

(51) Int. Cl.
| | | |
|---|---|---|
| *C07H 15/203* | (2006.01) | |
| *C07H 15/26* | (2006.01) | |
| *C07D 309/08* | (2006.01) | |
| *C07D 309/10* | (2006.01) | |

(52) U.S. Cl.
CPC ............ *C07D 309/08* (2013.01); *C07H 15/203* (2013.01); *C07H 15/26* (2013.01); *C07D 309/10* (2013.01)

(58) Field of Classification Search
None
See application file for complete search history.

(56) References Cited

U.S. PATENT DOCUMENTS

| | | | |
|---|---|---|---|
| 5,663,377 A | 9/1997 | Curley, Jr. et al. | |
| 6,069,238 A | 5/2000 | Hitchcock et al. | |
| 6,414,126 B1 | 7/2002 | Ellsworth et al. | |
| 6,515,117 B2 | 2/2003 | Ellsworth et al. | |
| 6,555,519 B2 | 4/2003 | Washburn | |
| 6,683,056 B2 | 1/2004 | Washburn et al. | |
| 6,774,112 B2 | 8/2004 | Gougoutas | |
| 6,936,590 B2 | 8/2005 | Washburn et al. | |
| 7,022,725 B2 | 4/2006 | Momose et al. | |
| 7,094,763 B2 | 8/2006 | Rybczynski et al. | |
| 7,371,732 B2 | 5/2008 | Eickelmann et al. | |
| 7,375,090 B2 | 5/2008 | Himmelsbach et al. | |
| 7,375,213 B2 | 5/2008 | Deshpande et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,838,498 B2 | 11/2010 | Chen et al. | |
| 7,838,499 B2 | 11/2010 | Chen et al. | |
| 2002/0111315 A1 | 8/2002 | Washburn et al. | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2004/0138148 A1 | 7/2004 | Fushimi et al. | |
| 2004/0138439 A1 | 7/2004 | Deshpande et al. | |
| 2004/0259819 A1 | 12/2004 | Frick et al. | |
| 2005/0014704 A1 | 1/2005 | Frick et al. | |
| 2005/0032712 A1 | 2/2005 | Urbanski | |
| 2005/0037980 A1 | 2/2005 | Rybczynski et al. | |
| 2005/0187168 A1 | 8/2005 | Eickelmann et al. | |
| 2005/0209166 A1 | 9/2005 | Eckhardt et al. | |
| 2005/0209309 A1 | 9/2005 | Sato et al. | |
| 2005/0233982 A1 | 10/2005 | Himmelsbach et al. | |
| 2005/0233988 A1 | 10/2005 | Nomura et al. | |
| 2006/0009400 A1 | 1/2006 | Eckhardt et al. | |
| 2006/0019948 A1 | 1/2006 | Eckhardt et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2006/0074031 A1 | 4/2006 | Eckhardt et al. | |
| 2006/0122126 A1 | 6/2006 | Imamura et al. | |
| 2006/0142210 A1 | 6/2006 | Eckhardt et al. | |
| 2006/0166899 A1 | 7/2006 | Teranishi et al. | |
| 2006/0189548 A1 | 8/2006 | Himmelsbach et al. | |
| 2006/0234953 A1 | 10/2006 | Himmelsbach et al. | |
| 2006/0234954 A1 | 10/2006 | Urbanski | |
| 2006/0235062 A1 | 10/2006 | Neogi et al. | |
| 2006/0247179 A1 | 11/2006 | Fushimi et al. | |
| 2006/0251728 A1 | 11/2006 | Himmelsbach et al. | |
| 2006/0258749 A1 | 11/2006 | Eckhardt et al. | |
| 2007/0004648 A1 | 1/2007 | Himmelsbach et al. | |
| 2007/0027092 A1 | 2/2007 | Himmelsbach et al. | |
| 2007/0049537 A1 | 3/2007 | Eckhardt et al. | |
| 2007/0054867 A1 | 3/2007 | Eckhardt et al. | |

(Continued)

FOREIGN PATENT DOCUMENTS

| | | | |
|---|---|---|---|
| CA | 2 539 032 A1 | 3/2005 | |
| CA | 2 548 353 A1 | 7/2005 | |
| EP | 1 489 089 A1 | 12/2004 | |
| EP | 1 783 110 A1 | 5/2007 | |
| EP | 1 803 721 A1 | 7/2007 | |
| EP | 1 852 439 A1 | 11/2007 | |
| EP | 1 908 757 A1 | 4/2008 | |

(Continued)

OTHER PUBLICATIONS

Isaji, "Sodium-glucose cotransporter inhibitors for diabetes," *Current Opinion in Investigational Drugs*, 2007, vol. 8, No. 4, pp. 285-292.

Standard Chemical Glossary (Japanese text), Maruzen K.K., Oct. 10, 1998, the 4th impression, p. 683.

*Primary Examiner* — Eric Olson

(74) *Attorney, Agent, or Firm* — Kilpatrick Townsend & Stockton LLP; William B. Kezer

(57) ABSTRACT

Provided are processes for the preparation of complexes that are useful in purifying compounds having an inhibitory effect on sodium-dependent glucose cotransporter SGLT. The processes can reduce the number of steps needed to obtain the target compounds and the complexes formed in the processes are typically provided in a crystalline form.

7 Claims, 3 Drawing Sheets

(56) References Cited

U.S. PATENT DOCUMENTS

| | | | |
|---|---|---|---|
| 2007/0072896 A1 | 3/2007 | Khan et al. | |
| 2007/0161787 A1 | 7/2007 | Imamura et al. | |
| 2007/0185197 A1 | 8/2007 | Fujikura et al. | |
| 2007/0197450 A1 | 8/2007 | Fushimi et al. | |
| 2007/0249544 A1 | 10/2007 | Himmelsbach et al. | |
| 2007/0275907 A1 | 11/2007 | Chen et al. | |
| 2008/0004336 A1 | 1/2008 | Gougoutas et al. | |
| 2008/0027014 A1 | 1/2008 | Nomura et al. | |
| 2008/0132563 A1 | 6/2008 | Kakinuma et al. | |
| 2008/0139484 A1 | 6/2008 | Teranishi et al. | |
| 2008/0318874 A1 | 12/2008 | Matsuoka et al. | |
| 2009/0023913 A1 | 1/2009 | Eckhardt et al. | |
| 2009/0118201 A1 | 5/2009 | Chen et al. | |
| 2010/0063141 A1 | 3/2010 | Seed et al. | |
| 2012/0238510 A1* | 9/2012 | Cai et al. | 514/23 |
| 2014/0011754 A9* | 1/2014 | Cai et al. | 514/23 |

FOREIGN PATENT DOCUMENTS

| | | | |
|---|---|---|---|
| EP | 2 009 010 A1 | 12/2008 | |
| WO | 98/31697 A1 | 7/1998 | |
| WO | 01/27128 A1 | 4/2001 | |
| WO | 01/74834 A1 | 10/2001 | |
| WO | 01/74835 A1 | 10/2001 | |
| WO | 02/083066 A2 | 10/2002 | |
| WO | 02/083066 A3 | 10/2002 | |
| WO | 03/020737 A1 | 3/2003 | |
| WO | 03/099836 A1 | 12/2003 | |
| WO | 2004/063209 A2 | 7/2004 | |
| WO | 2004/063209 A3 | 7/2004 | |
| WO | 2005/021566 A2 | 3/2005 | |
| WO | 2005/021566 A3 | 3/2005 | |
| WO | 2005/063785 A2 | 7/2005 | |
| WO | 2005/063785 A3 | 7/2005 | |
| WO | 2005/085237 A1 | 9/2005 | |
| WO | 2005/092877 A1 | 10/2005 | |
| WO | 2006/002912 A1 | 1/2006 | |
| WO | 2006/008038 A1 | 1/2006 | |
| WO | 2006/010557 A1 | 2/2006 | |
| WO | 2006/011469 A1 | 2/2006 | |
| WO | 2006/018150 A1 | 2/2006 | |
| WO | 2006/034489 A2 | 3/2006 | |
| WO | 2006/034489 A3 | 3/2006 | |
| WO | 2006/037537 A2 | 4/2006 | |
| WO | 2006/037537 A3 | 4/2006 | |
| WO | 2006/064033 A2 | 6/2006 | |
| WO | 2006/064033 A3 | 6/2006 | |
| WO | 2006/073197 A1 | 7/2006 | |
| WO | 2006/080421 A1 | 8/2006 | |
| WO | WO2006/089872 A1 | 8/2006 | |
| WO | 2006/108842 A1 | 10/2006 | |
| WO | 2006/110654 A1 | 10/2006 | |
| WO | 2006/117359 A1 | 11/2006 | |
| WO | 2006/117360 A1 | 11/2006 | |
| WO | 2006/120208 A1 | 11/2006 | |
| WO | 2007/000445 A1 | 1/2007 | |
| WO | 2007/014894 A2 | 2/2007 | |
| WO | 2007/014894 A3 | 2/2007 | |
| WO | 2007/025943 A2 | 3/2007 | |
| WO | 2007/025943 A3 | 3/2007 | |
| WO | 2007/028814 A1 | 3/2007 | |
| WO | 2007/114475 A1 | 10/2007 | |
| WO | 2007/136116 A2 | 11/2007 | |
| WO | 2007/136116 A3 | 11/2007 | |
| WO | 2008/002824 A1 | 1/2008 | |
| WO | 2008/049923 A1 | 5/2008 | |
| WO | 2008/069327 A1 | 6/2008 | |
| WO | 2009/026537 A1 | 2/2009 | |
| WO | 2009/035969 A1 | 3/2009 | |

* cited by examiner

Scheme I

PROCESSES FOR THE PREPARATION OF SGLT2 INHIBITORS

CROSS-REFERENCES TO RELATED APPLICATIONS

This application claims the benefit of U.S. Ser. No. 61/091,248 filed Aug. 22, 2008, the contents of each are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

According to the World Health Organization, approximately 150 million people worldwide have diabetes mellitus. The two principle forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

Compounds which inhibit SGLT, particularly SGLT2, are currently under clinical evaluation for use as antidiabetic drugs. Compounds previously described as useful for inhibiting SGLT include C-glycoside derivatives (such as those described in U.S. Pat. No. 6,414,126, US20040138439, US20050209166, US20050233988, WO2005085237, U.S. Pat. No. 7,094,763, US20060009400, US20060019948, US20060035841, US20060122126, US20060234953, WO2006108842, US20070049537 and WO2007136116), O-glycoside derivatives (such as those described in U.S. Pat. No. 6,683,056, US20050187168, US20060166899, US20060234954, US20060247179 and US20070185197), spiroketal-glycoside derivatives (described in WO2006080421), cyclohexane derivatives (such as those described in WO2006011469), and thio-glucopyranoside derivatives (such as those described in US20050209309 and WO2006073197) In addition to the agents described in the noted references, new processes are needed for their synthesis that can improve upon current yields and provide compounds in crystalline form. Surprisingly, the present invention addresses such needs.

BRIEF SUMMARY OF THE INVENTION

The present invention provides methods of preparing compounds having an inhibitory effect on sodium-dependent glucose cotransporter SGLT. The invention also provides crystalline forms of the compounds and further describes pharmaceutical compositions, synthetic intermediates, and methods of using the compounds, independently or in combination with other therapeutic agents, for treating diseases and conditions which are affected by SGLT inhibition.

DETAILED DESCRIPTION OF THE INVENTION

Definitions

Figure 1:
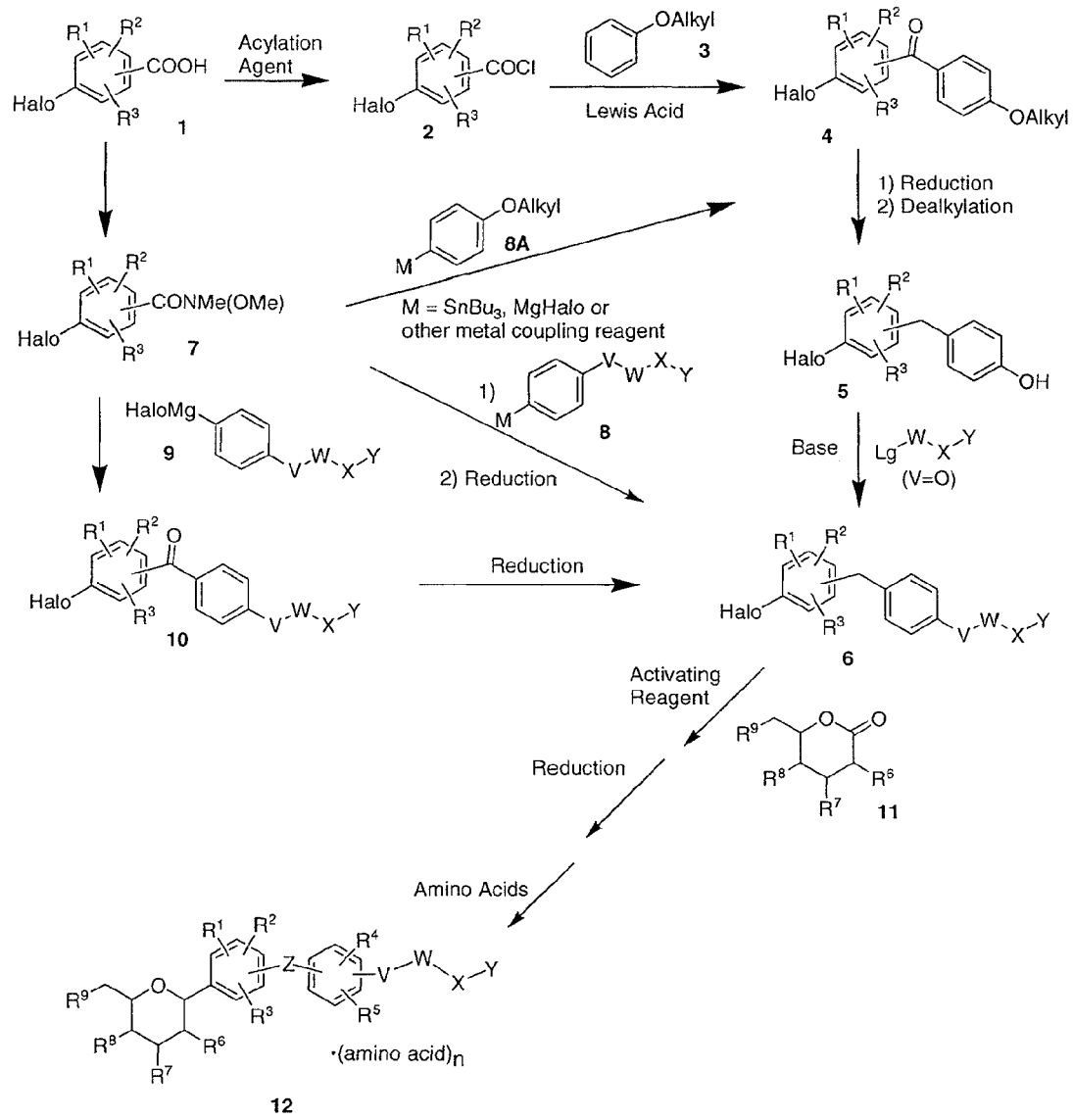
FIG. 1 is the general synthesis method of Scheme I for the preparation of compounds of the invention.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons forming a carbocyclic ring and at least one carbon-carbon double bond and, where specified, optionally substituted with one to three suitable substituents as defined above.

Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the terms "alkylene", "alkenylene", "cycloalkylene" and "cycloalkenylene" refer to a divalent hydrocarbon radical that is formed by removal of a hydrogen atom from an alkyl, alkenyl, cycloalkyl or cycloalkenyl radical, respectively, as such terms are defined above.

As used herein, the term "($C_3$-$C_{10}$ cycloalkylene)($C_1$-$C_6$ alkylene)" refers to a divalent hydrocarbon radical that is formed by bonding a $C_3$-$C_{10}$ cycloalkylene radical with $C_1$-$C_6$ alkylene radical, as such terms are defined above.

As used herein, unless otherwise indicated, the term "aryl" alone or in combination refers to a monovalent aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, 21$^{st}$ Ed., Gennaro, Ed., Lippencott Williams & Wilkins (2003). As discussed therein, immediate and nonimmediate release can be defined kinetically by reference to the following equation:

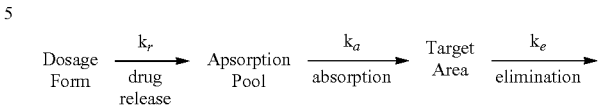

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

General

The present invention provides processes for the preparation of intermediate complexes that can be readily converted to compounds having an inhibitory effect on sodium-dependent glucose cotransporter SGLT, preferably SGLT2. In some instances, the complexes themselves have activity as inhibitors of SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the intermediate complexes and compounds prepared by the methods herein are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The methods of the present invention are particularly useful as they represent an efficient process for the preparation of SGLT2 inhibitors. In contrast to the methods described in US 2004/0138439, the methods of the present invention involve the reduction of an intermediate followed by complex formation with an amino acid, wherein the complex is solid, typically crystalline, and can be formed on large scale without intervening protection and deprotection steps. By removing the protection and deprotection steps, the final product can be produced in higher yield and in the absence of solvent impurities (e.g., pyridine) that are difficult to remove with the known processes. Still further, contaminants resulting from incomplete deprotection (for example, a mono-acetylated intermediate) that can be difficult to remove are avoided.

Overall, the present methods provide benefits of increased yield, speed and reduced cost (owing to a reduced number of steps) and decreased solvent consumption; and further minimizes impurities from entrapped solvent and intermediates. Still further, formation of the complex of Formula I can be carried out without purification of the compound of Formula II.

The present invention also provides crystalline forms of amino acid complexes of the parent SGLT2 inhibitors.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

DETAILED EMBODIMENTS

Compounds and Preparative Methods

In one aspect, the present invention provides methods for the preparation of a complex of Formula I:

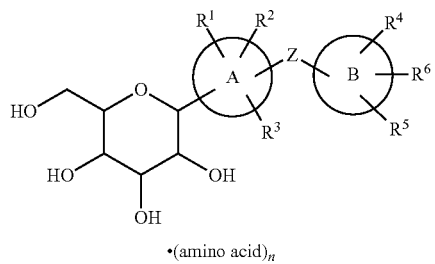

(I)

•(amino acid)$_n$ wherein the subscript n is 1 or 2;

the rings designated by A and B are each independently an aromatic or heteroaromatic ring or fused-ring system, selected from the group consisting of benzene, naphthalene, pyrazole, oxazole, oxadiazole, imidazole, thiazole, thiadiazole, triazole, thiophene, furan, pyridine, pyridazine, pyrimidine, pyrazine, benzotriazole, benzimidazole, indole, indazole, triazolopyridine, triazolopyrimidine, purine, quinoline, isoquinoline, cinnoline, phthalazine, quinazoline, quinoxaline, 1,5-naphthyridine, 1,6-naphthyridine, benzothiophene, benzofuran and benzothiazole;

$R^1$, $R^2$ and $R^3$ are each members independently selected from the group consisting of hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, cyano and nitro, wherein alkyl and cycloalkyl groups or portions are optionally mono- or polysubstituted by fluorine, or when $R^1$ and $R^2$ are bound to two adjacent C atoms, $R^1$ and $R^2$ are optionally joined together to form a $C_3$-$C_5$ alkylene, $C_3$-$C_5$ alkenylene or butadienylene bridge, which is optionally partly or completely fluorinated and is optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups are optionally replaced by N; or optionally, one or more of $R^1$, $R^2$ and $R^3$ are absent;

$R^4$, $R^5$ and $R^6$ are each members independently selected from the group consisting of hydrogen, halo, cyano, nitro, hydroxy, $C_1$-$C_6$ alkyl, $C_3$-$C_{10}$ cycloalkyl, $C_1$-$C_3$ alkyloxy and $C_3$-$C_{10}$ cycloalkyloxy, wherein alkyl and cycloalkyl groups or portions are optionally mono- or polysubstituted by fluorine, or when $R^4$ and $R^5$ are bound to two adjacent C atoms, $R^4$ and $R^5$ are optionally joined together to form a $C_3$-$C_5$ alkylene, $C_3$-$C_5$ alkenylene or butadienylene bridge, which is optionally partly or completely fluorinated and is optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups are optionally replaced by N; or optionally, one or more of $R^4$, $R^5$ and $R^6$ are absent;

optionally, one of $R^3$ and $R^6$ is —V—W—X—Y, wherein
V is a member selected from the group consisting of oxygen; sulfur; SO; $SO_2$; and a single bond;

W is a member selected from the group consisting of $C_1$-$C_6$ alkylene, $C_2$-$C_6$ alkenylene, $C_2$-$C_6$ alkynylene, $C_3$-$C_{10}$ cycloalkylene, $C_5$-$C_{10}$ cycloalkenylene and ($C_3$-$C_{10}$ cycloalkylene)($C_1$-$C_6$ alkylene) wherein the $C_3$-$C_{10}$ cycloalkylene portion bonds to V and the $C_1$-$C_6$ alkylene portion bonds to X, and wherein alkylene, alkenylene, alkynylene, cycloalkylene and cycloalkenylene groups or portions are optionally partly or completely fluorinated and are optionally mono- or disubstituted by substituents independently selected from the group consisting of chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl and $C_5$-$C_{10}$ cycloalkenyloxy, and in cycloalkylene and cycloalkenylene groups or portions one or two methylene groups are optionally replaced independently of one another by O, S, CO, SO, $SO_2$ or $NR^b$, and one or two methyne groups are optionally replaced by N;

X is a member selected from the group consisting of a single bond; oxygen; sulfur; $NR^a$, SO; and $SO_2$;

Y is a member selected from the group consisting of hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_3$-$C_{10}$ cycloalkyl)$C_1$-$C_4$ alkyl, ($C_5$-$C_{10}$ cycloalkenyl)$C_1$-$C_3$ alkyl, ($C_3$-$C_{10}$ cycloalkyl)$C_2$-$C_4$ alkenyl, $C_3$-$C_6$ cycloalkylidenmethyl, ($C_5$-$C_{10}$ cycloalkenyl)$C_2$-$C_4$ alkenyl, ($C_1$-$C_4$ alkyloxy)$C_1$-$C_3$ alkyl, ($C_2$-$C_4$ alkenyloxy)$C_1$-$C_3$ alkyl, ($C_3$-$C_{10}$ cycloalkyloxy)$C_1$-$C_3$ alkyl, ($C_5$-$C_{10}$ cycloalkenyloxy)$C_1$-$C_3$ alkyl, (amino)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_6$ alkyl)carbonyl($C_1$-$C_3$)alkyl, ($C_2$-$C_6$ alkenyl)carbonyl ($C_1$-$C_3$)alkyl, ($C_2$-$C_6$ alkynyl)carbonyl($C_1$-$C_3$)alkyl, (arylcarbonyl)$C_1$-$C_3$ alkyl, (heteroarylcarbonyl)$C_1$-$C_3$ alkyl, ($C_1$-$C_6$ alkylsulfonyl)$C_1$-$C_3$ alkyl, ($C_2$-$C_6$ alkenylsulfonyl)$C_1$-$C_3$ alkyl, ($C_2$-$C_6$ alkynylsulfonyl)$C_1$-$C_3$ alkyl, (arylsulfonyl)$C_1$-$C_3$ alkyl, (heteroarylsulfonyl)$C_1$-$C_3$ alkyl, ($C_1$-$C_6$ alkyl)aminocarbonyl($C_1$-$C_3$)alkyl, ($C_2$-$C_6$ alkenyl)aminocarbonyl($C_1$-$C_3$)alkyl, ($C_2$-$C_6$ alkynyl)aminocarbonyl($C_1$-$C_3$)alkyl, (arylaminocarbonyl)$C_1$-$C_3$ alkyl, (heteroarylaminocarbonyl)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, arylcarbonyl, heteroarylcarbonyl, ($C_1$-$C_6$ alkyl)sulfonyl, ($C_2$-$C_6$ alkenyl)sulfonyl, ($C_2$-$C_6$ alkynyl)sulfonyl, arylsulfonyl, heteroarylsulfonyl, $C_1$-$C_6$ alkylsulfinyl, arylsulfinyl, heteroarylsulfinyl, ($C_1$-$C_6$ alkyl)aminocarbonyl, ($C_2$-$C_6$ alkenyl)aminocarbonyl, ($C_2$-$C_6$ alkynyl)aminocarbonyl, arylaminocarbonyl, heteroarylaminocarbonyl, ($C_1$-$C_6$ alkylsulfinyl)$C_1$-$C_3$ alkyl, (arylsulfinyl)$C_1$-$C_3$ alkyl, (heteroarylsulfinyl)$C_1$-$C_3$ alkyl, wherein alkyl, alkenyl, alkynyl, cycloalkyl and cycloalkenyl groups or portions are optionally partly or completely fluorinated and are optionally mono- or disubstituted by substituents independently selected from the group consisting of chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl, $C_5$-$C_{10}$ cycloalkenyloxy, and $NR^bR^c$, and in cycloalkyl and cycloalkenyl groups or portions one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl;

Z is a member selected from the group consisting of oxygen; sulfur; SO; $SO_2$; 1,1-cyclopropylene; carbonyl; and methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^a$ is a member independently selected from the group consisting of H, $C_1$-$C_6$ alkyl, $C_3$-$C_6$ cycloalkyl and ($C_1$-$C_4$ alkyl)carbonyl, wherein alkyl and cycloalkyl groups or portions are optionally partly or completely fluorinated;

each $R^b$ is a member independently selected from the group consisting of H, $C_1$-$C_4$ alkyl and ($C_1$-$C_4$ alkyl)carbonyl, wherein alkyl groups or portions are optionally partly or completely fluorinated;

each $R^c$ is a member independently selected from the group consisting of H, $C_1$-$C_4$ alkyl, $C_3$-$C_6$ cycloalkyl, $CHR^dR^e$, $SO_2R^d$, $C(O)OR^d$ and $C(O)NR^dR^e$, wherein alkyl and cycloalkyl groups are optionally partly or completely fluorinated; and $R^d$ and $R^e$ each independently represent H or $C_1$-$C_6$ alkyl, wherein alkyl groups are optionally partly or completely fluorinated;

and pharmaceutically acceptable salts thereof;
comprising:
(a) reacting a compound of Formula II

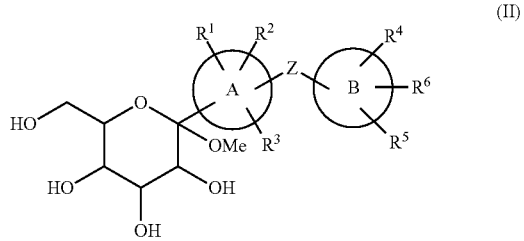

with a reducing agent in the presence of an activating group to form a compound of Formula III

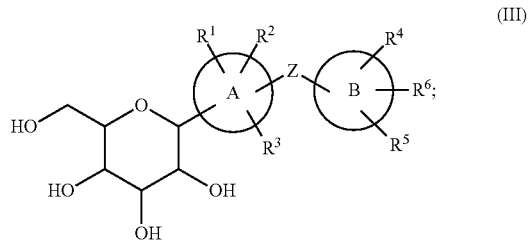

and
(b) contacting said compound of Formula III with an amino acid to form said complex of Formula I;

wherein steps (a) and (b) are performed without purification of said compound of Formula III and wherein steps (a) and (b) are performed sequentially without an intervening protection or deprotection step.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, II and III, either in admixture or in pure or substantially pure form. The compounds of the present invention can have asymmetric centers at the carbon atoms, and therefore the compounds of Formula I can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds prepared according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides methods for preparing prodrugs of compounds of Formula I. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino($C_2$-$C_3$)alkyl (e.g., beta-dimethylaminoethyl), carbamoyl-$(C_1$-$C_2)$alkyl, N,N-di$(C_1$-$C_2)$alkylcarbamoyl-$(C_1$-$C_2)$alkyl and piperidino-, pyrrolidino- or morpholino $(C_2$-$C_3)$alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The method of the present invention derives from the surprising discovery that amino acid complexes of Formula I can be prepared and isolated, typically as crystalline solids without protection and deprotection steps following the reduction of a compound of Formula II into a compound of Formula III. Still further, the method can be applied to crude reaction mixtures, wherein compounds of Formula III are treated with an amino acid to form the desired complex, without purification of the compound of Formula III.

Turning now to the inventive methods, compounds of Formula II can serve as starting materials and can be obtained by methods known to those of skill in the art (see, for example, US 2008/0004336, WO 2008/002824, US 2006/0258749, US 2005/0209166, US 2004/0138439, US 2003/0064935, U.S. Ser. No. 12/060,767, and US 2009/0118201 and as provided in the Examples below. Preferably, the compounds of Formula II are provided as solids, although oils and solutions of the compounds are also suitable.

In step (a), the compounds of Formula II are reacted with a reducing agent in the presence of an activating group to form a compound of Formula III. Generally, the reducing agent is a silane reducing agent, more particularly an alkylsilyl hydride such as triethylsilane or triisopropylsilane. The reaction is typically carried out in the presence of an activating agent such as a Lewis acid, with $BF_3.Et_2O$ (boron trifluoride etherate) being preferred.

One of skill in the art will appreciate that a variety of conditions can be employed for the reduction of compounds of Formula II to compounds of Formula III. Generally, the reactions are carried out in compatible aprotic solvents such as dichloromethane, acetonitrile, dichloroethane, chloroform and toluene, as well as solvent mixtures. In certain preferred embodiments, the starting material (compounds of Formula II) in solvent is cooled to 0° C. or less and the reducing agent and activating agent are added gradually to the starting material. The reducing agent and activating agent are added in excess (from 1.1 equivalents to about 6 equivalents based on the amount of the compound of Formula II), typically a 20%, 40%, 80%, 100%, 200%, 300% or 400% excess, or more. The reaction can be stirred with cooling or can be gradually warmed (generally to room temperature) and monitored until no further loss of starting material is observed.

When the reaction is sufficiently complete, excess reducing agent is quenched with a careful addition of, for example, sodium bicarbonate. The quenching agent can be added as a solid, although an aqueous solution of the agent (sodium bicarbonate) is generally used. Workup methods (evaporation of solvent, extraction/partitioning with organic solvent, washing, drying) are usually employed to provided the crude product of Formula III that can converted to the complex of Formula I without additional purification methods (e.g., chromatography, recrystallization).

Turning next to step (b), the compound of Formula III is contacted with an amino acid in an amount sufficient to form the complex of Formula I. A variety of amino acids are useful in the present invention, including for example, the natural amino acids, preferably chiral forms of natural amino acids. In certain preferred embodiments, the amino acid is selected from D-proline, L-proline, D-phenylalanine, L-phenylalanine, D-aspartamine, and L-aspartamine. The amount of amino acid used for complex formation will depend on the ratio of amino acid to compound in the desired complex. Generally, a slight excess of amino acid is used. For example, to prepare complexes of Formula I wherein n is 2, about 2.0 to 3.0 equivalents of amino acid (relative to the compound of Formula III) are used. Preferably, about 2.0 to 2.5 equivalents of amino acid are used. Step (b) is generally carried out in a solvent or a mixture of solvents. One suitable solvent mixture includes ethanol and water, with added hexane or heptane.

The present invention also provides for the pharmaceutically acceptable salts of compounds of Formula I and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds of Formula I and prodrugs thereof, as well as isotopically-labeled, pharmaceutically acceptable salts of compounds of Formula I and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

In preferred embodiments, one of $R^3$ and $R^6$ is —V—W—X—Y, wherein V represents oxygen, sulfur, or a single bond.

In particularly preferred embodiments, one of $R^3$ and $R^6$ is —V—W—X—Y, wherein V represents oxygen or a single bond.

In preferred embodiments, one of $R^3$ and $R^6$ is —V—W—X—Y, wherein W represents $C_1$-$C_6$ alkylene, $C_2$-$C_6$ alkenylene, $C_2$-$C_6$ alkynylene, $C_3$-$C_{10}$ cycloalkylene, or ($C_3$-$C_{10}$ cycloalkylene)($C_1$-$C_6$ alkylene). In particularly preferred embodiments, one of $R^3$ and $R^6$ is —V—W—X—Y, wherein W represents $C_1$-$C_6$ alkylene, $C_2$-$C_6$ alkenylene, $C_2$-$C_6$ alkynylene, or $C_3$-$C_{10}$ cycloalkylene. In each of these groups of embodiments, alkylene, alkenylene, alkynylene, cycloalkylene and cycloalkenylene groups or portions are optionally partly or completely fluorinated and are optionally mono- or disubstituted by substituents independently selected from the group consisting of chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl and $C_5$-$C_{10}$ cycloalkenyloxy, and in cycloalkylene and cycloalkenylene groups or portions one or two methylene groups are optionally replaced independently of one another by O, S, CO, SO, $SO_2$ or $NR^b$, and one or two methyne groups are optionally replaced by N;

In preferred embodiments, one of $R^3$ and $R^6$ is —V—W—X—Y, wherein X represents oxygen, sulfur, a single bond, or $NR^a$.

In preferred embodiments, one of $R^3$ and $R^6$ is —V—W—X—Y, wherein Y represents hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_4$ alkyl, ($C_1$-$C_4$ alkyloxy)$C_1$-$C_3$ alkyl, ($C_3$-$C_{10}$ cycloalkyloxy)$C_1$-$C_3$ alkyl, (amino)$C_1$-$C_3$ alkyl, ($C_1$-$C_4$ alkylamino)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, ($C_1$-$C_6$ alkyl)sulfonyl, ($C_2$-$C_6$ alkenyl)sulfonyl, or ($C_2$-$C_6$ alkynyl)sulfonyl, wherein alkyl, alkenyl, alkynyl and cycloalkyl groups or portions optionally may be partly or completely fluorinated and may be mono- or disubstituted by identical or different substituents selected from chlorine, hydroxy, $C_1$-$C_3$ alkyl, $C_1$-$C_3$ alkoxy, and $C_3$-$C_6$ cycloalkyl, and in cycloalkyl groups or portions one or two methylene groups are optionally replaced independently of one another by O, S, CO, SO, $SO_2$ or $NR^b$, and one or two methyne groups are optionally replaced by N. In particularly preferred embodiments, one of $R^3$ and $R^6$ is —V—W—X—Y, wherein Y represents hydrogen, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, or ($C_1$-$C_4$ alkyloxy)$C_1$-$C_3$ alkyl.

In preferred embodiments, one of $R^3$ and $R^6$ is —V—W—X—Y, and Z represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Z represents methylene.

In preferred embodiments, $R^1$, $R^2$ and $R^3$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^1$, $R^2$ and $R^3$ each independently represent hydrogen, halo or $C_1$-$C_6$ alkyl. In more particularly preferred embodiments, $R^1$ represents hydrogen, halo or $C_1$-$C_6$ alkyl and $R^2$ and $R^3$ both represent hydrogen.

In preferred embodiments, $R^4$ and $R^5$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^4$ and $R^5$ each independently represent hydrogen, halo or $C_1$-$C_6$ alkyl. In more particularly preferred embodiments, $R^4$ and $R^5$ both represent hydrogen.

Formula IA represents still other preferred embodiments:

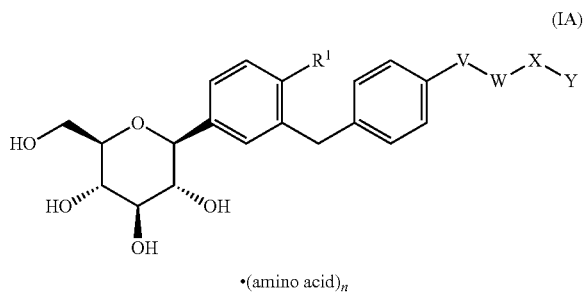

(IA)

•(amino acid)$_n$ wherein $R^1$ represents hydrogen, halo or $C_1$-$C_6$ alkyl; V represents oxygen or a single bond; W represents $C_1$-$C_6$ alkylene, $C_2$-$C_6$ alkenylene, $C_2$-$C_6$ alkynylene, $C_3$-$C_{10}$ cycloalkylene, or ($C_3$-$C_{10}$ cycloalkylene)($C_1$-$C_6$ alkylene); X represents oxygen, a single bond, or $NR^a$; and Y represents hydrogen, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_4$ alkyl, ($C_1$-$C_4$ alkyloxy)$C_1$-$C_3$ alkyl, ($C_3$-$C_{10}$ cycloalkyloxy)$C_1$-$C_3$ alkyl, (amino)$C_1$-$C_3$ alkyl, ($C_1$-$C_4$ alkylamino)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, ($C_1$-$C_6$ alkyl)sulfonyl, ($C_2$-$C_6$ alkenyl)sulfonyl, or ($C_2$-$C_6$ alkynyl)sulfonyl, wherein alkyl, alkenyl, alkynyl and cycloalkyl groups or portions optionally may be partly or completely fluorinated and may be mono- or disubstituted by identical or different substituents selected from chlorine, hydroxy, $C_1$-$C_3$ alkyl, $C_1$-$C_3$ alkoxy, and $C_3$-$C_6$ cycloalkyl, and in cycloalkyl groups or portions one or two methylene groups are optionally replaced independently of one another by O, S, CO, SO, $SO_2$ or $NR^b$, and one or two methyne groups are optionally replaced by N.

In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In addition to the processes and methods above, more detailed particular examples are presented below in the experimental section describing the working examples. By following the general preparative methods, or employing variations, the compounds of Formula I can be readily prepared by the those of skill in the art.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: Ac$_2$O, acetic anhydride; AcOEt, ethyl acetate; AcOH, acetic acid; AIBN, azobis(isobutyronitrile); AlBr$_3$, aluminum bromide; AlCl$_3$, aluminum chloride; BBr$_3$, boron tribromide; BF$_3$.Et$_2$O, boron trifluoride etherate; BTEAC, benzyltriethylammonium chloride; n-BuLi, n-butyllithium; s-BuLi, s-butyllithium; t-BuLi, t-butyllithium; t-BuOK, potassium tert-butoxide; CaCl$_2$, calcium chloride; calc., calculated; CCl$_4$, carbon tetrachloride; CD$_3$OD, methanol-d$_4$; CDCl$_3$, chloroform-d; CF$_3$SO$_3$H, trifluoromethanesulfonic acid; CH$_2$Cl$_2$, methylene chloride; CH$_2$I$_2$, methylene iodide; CH$_3$CN, acetonitrile; (COCl)$_2$, oxalyl chloride; Cs$_2$CO$_3$, cesium carbonate; DAST, (diethylamino)sulfur trifluoride; DCM, dichloromethane; DMAP, 4-dimethylaminopyridine; DMEM, Dulbecco's Modified Eagle Medium; DMF, N,N-dimethylformamide; DMP, Dess-Martin periodinane; DMSO, dimethylsulfoxide; EA, ethyl acetate; EDCI, 1-(3-dimethylaminopropyl)-3-ethylcarbodiimide hydrochloride; eq, equivalents; Et, ethyl; Et$_3$N, triethylamine; Et$_3$SiH, triethylsilane; Et$_3$SiO, triethylsilyloxy; EtOAc, ethyl acetate; EtOH, ethanol; FBS, fetal bovine serum; FSO$_2$CF$_2$CO$_2$H, 2,2-difluoro-2-(fluorosulfonyl)acetic acid; h, hour; H$_2$, hydrogen gas; H$_2$SO$_4$, sulfuric acid; Hepes, 4-(2-hydroxyethyl)-1-piperazineethanesulfonic acid; $^1$H NMR, proton nuclear magnetic resonance; HOBt, 1-hydroxybenzotriazole; HPLC, high performance liquid chromatography; K$_2$CO$_3$, potassium carbonate; K$_2$CrO$_7$, potassium dichromate; KN(TMS)$_2$, potassium bis(trimethylsilyl)amide; KOH, potassium hydroxide; LC-ESI-MS, liquid chromatography electrospray ionization mass spectrometry; LC-MS, liquid chromatography-mass spectroscopy; Lg, leaving group; LiOH.H$_2$O, lithium hydroxide monohydrate; Me, methyl; MeCN, acetonitrile; MeOH, methanol; MeSO$_3$H, methanesulfonic acid; Mg, magnesium; MgCl$_2$, magnesium chloride; min, minute; MS ESI, mass spectroscopy with electrospray ionization; MsOH, methanesulfonic acid; NaBH$_3$CN, sodium cyanoborohydride; NaH, sodium hydride; NaHCO$_3$, sodium bicarbonate; NaHSO$_3$, sodium bisulfate; NaOAc, sodium acetate; NaOH, sodium hydroxide; Na$_2$SO$_4$, sodium sulfate; NBS, N-bromosuccinimide; NCS, N-chlorosuccinimide; NH$_4$Cl, ammonium chloride; NIS, N-iodosuccinimide; O$_3$, ozone; Pd/C, palladium on carbon; PdCl$_2$, palladium (II) chloride; PE, petroleum ether; Ph, phenyl; Ph$_3$PCH$_3$I (or Ph$_3$PMeI), methyltriphenylphosphonium iodide; POCl$_3$, phosphorus oxychloride; PPh$_3$, triphenylphosphine; R$_f$, retention factor; SnBu$_3$, tributyltin; SOCl$_2$, thionyl chloride; TBAI, tetrabutylammonium iodide; TFA, trifluoroacetic acid; THF, tetrahydrofuran; TLC, thin layer chromatography; TMS, trimethylsilyl; TMSCN, trimethylsilyl cyanide; Tris, trishydroxymethylaminomethane (or 2-amino-2-(hydroxymethyl)propane-1,3-diol); TsCl, toluenesulfonyl chloride; TsOH, toluenesulfonic acid; ZnEt$_2$, diethyl zinc.

The element deuterium is represented by the letter "D" in chemical structures and formulae and indicated with a lower case "d" in chemical names, according to the Boughton system.

General Synthesis Method of Scheme I

Inventive compounds of formula 12 can be conveniently prepared according to the reaction sequences as shown in Scheme I (FIG. 1). Acid 1, which may be commercially available or prepared according to conventional methods known to those of skill in the art, is converted to acid chloride 2 by an agent such as oxalyl chloride, SOCl$_2$, POCl$_3$ or the like. Intermediate 2 is reacted with alkoxybenzene 3 under conditions aided by Lewis acid, such as AlCl$_3$ or AlBr$_3$, to provide ketone 4. The ketone group of intermediate 4 is reduced to methylene with a reducing agent such as Et$_3$SiH in the present of a Lewis acid such as BF$_3$.Et$_2$O or TFA, and treatment with Lewis acid such as BBr$_3$ to give phenol 5. Intermediate 6 can be obtained by coupling with the electrophilic reagent Lg-W—X—Y, where Lg denotes a suitable leaving group, in the presence of base such as K$_2$CO$_3$, Cs$_2$CO$_3$, NaOH or the like.

Alternatively, acid 1 can be converted to Weinreb amide 7 or other equivalent amides by coupling with NHMe(OMe) or other equivalent amines. Intermediate 4 can then be obtained by treatment of the resulting amide 7 with intermediate 8, bearing a metal coupling reagent such as Grignard reagent.

Alternatively, intermediate 6 can also be obtained by coupling of the amide 7 with Grignard reagent 9, followed by reduction of the ketone group of product 10 with Et$_3$SiH in the presence a Lewis acid such as BF$_3$.Et$_2$O or TFA.

Intermediate 6 is condensed with ketone 11 (wherein R$^6$, R$^7$, R$^8$ and R$^9$ are -OTMS) after treatment with activating reagent, such as n-BuLi or t-BuOK to provide compounds of general Formula II which can then be reduced with alkylsilane or other reductant in the presence of acid, such as TFA, MeSO$_3$H or BF$_3$.Et$_2$O, to generate compounds of Formula III (e.g, 12 wherein R$^6$, R$^7$, R$^8$ and R$^9$ are —OH).

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science*, Vol. 88, No. 2, 25 Jan. 2005, pp. 241-249, and the like), glycogen phosphorylase inhibitors (such as N,N-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R.

K., et al., *Current Science*, Vol. 88, No. 2, 25 Jan. 2005, pp. 241-249, and the like), incretin mimetics (such as exenatide and the like), glucagon receptor antagonists (such as BAY-27-9955, N,N-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation endproducts (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, C1-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as, 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson BM, *J. Med. Chem.* 2006, 49:4023-4034)), beta-3 adrenergic receptor agonists (such as L-796568, CGP 12177, BRL-28410, SR-58611A, 1CI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, A-71378, FPL-15849, GI-248573, GW-7178, GI-181771, GW-7854, GW-5823, and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB 1 receptor antagonists (such as rimonabant and the like), melanin-concentrating hormone receptor antagonists (such as GlaxoSmithKline 856464, SNAP-7941, T-226296 and the like), and selective muscarinic receptor $M_1$ antagonists (such as telenzepine, pirenzepine and the like).

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and anti-platelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Gas chromatography—mass spectra with electrospray ionization (MS ESI) were obtained with an Agilent 5973N mass spectrometer equipped with an Agilent 6890 gas chromatograph with an HP-5 MS column (0.25 μm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 μm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% B to 90% in 8 min at a flow rate of 1.0 mL/min is used with a final hold at 90% B of 7 min. Total run time is 15 min.

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1

Preparation of (2S,3R,4R,5S,6R)-2-(4-chloro-3-(4-ethoxybenzyl)phenyl)-6-(hydroxymethyl)tetrahydro-2H-pyran-3,4,5-triol, bis(L-proline) complex (1D)

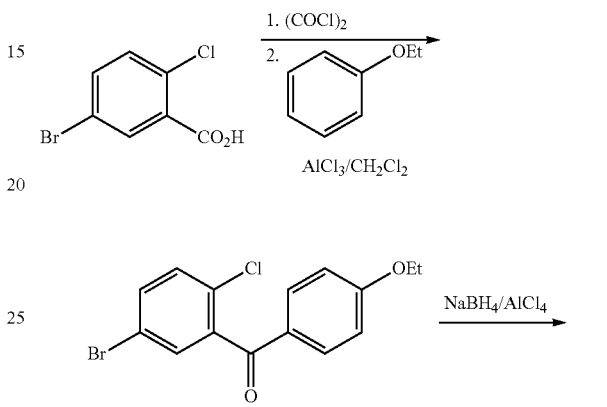

Example 1A

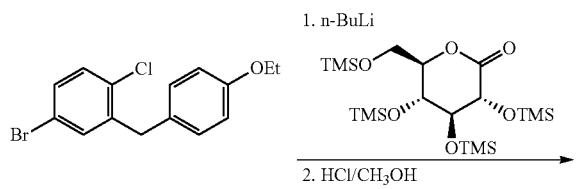

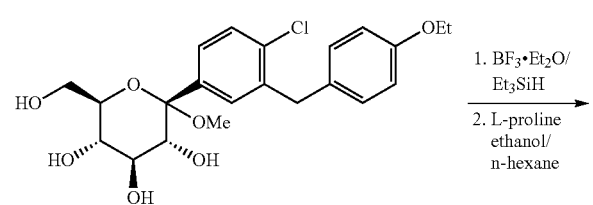

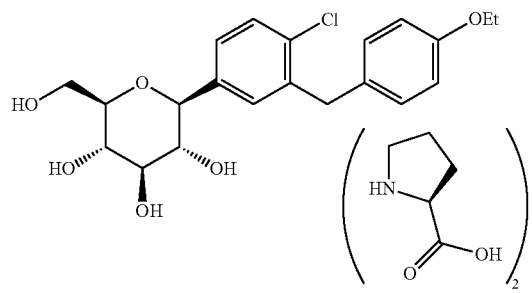

Example 1D

Examples 1A

Preparation of (5-bromo-2-chlorophenyl)(4-ethoxyphenyl)methanone

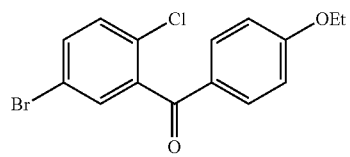 [SMILES: CCOc1ccc(C(=O)c2cc(Br)ccc2Cl)cc1]

N,N-Dimethylforamide (9 mL) was added to a suspension of 5-bromo-2-chlorobenzoic acid (1500 g, 6.41 mol) and oxalyl chloride (975 g, 7.69 mol) in a 5 L 4-necked flask containing dichloromethane (2.8 L) at room temperature. Once the vigorous evolution of gas ceased, the reaction was stirred for 10 h at room temperature. The reaction mixture was concentrated under vacuum to give a yellow residue. The residue was dissolved in dichloromethane (1.2 L) in a 5 L 4-necked flask equipped with an internal thermometer and a water condenser. The stirred mixture was cooled to −3° C. and phenetole (799 g, 6.54 mol) was added. Aluminum (III) chloride (973 g, 6.54 mol) was added to the above solution via a solid addition funnel over 1 h while maintaining the internal temperature below 4° C. After the addition was complete, the reaction mixture was stirred for 2 h at 5~10° C. The reaction was poured into ice (10 kg). The mixture was further stirred at 4° C. for 1 h, diluted with water (3 L), transferred to a 50 L extraction funnel and extracted with dichloromethane (10 L×2). The combined organic layers were washed with 1 N HCl (7.5 L×2), water (10 L), 1N sodium hydroxide (7.5 L×2), brine (10 L×2), dried over sodium sulfate (1000 g), and concentrated. The residue was recrystallized in absolute ethanol (3.5 L) to give the title compound as a white solid (1.450 kg, yield 67%, HPLC purity>99%). $^1$H NMR (CDCl$_3$, 400 MHz): δ 7.77 (d, J=9 Hz, 2H), 7.49-7.53 (m, 1H), 7.47 (d, J=2.1 Hz, 1H), 7.30 (d, J=9 Hz, 1H), 6.90 (d, J=9 Hz, 2H), 4.10 (q, J=7.2 Hz, 2H), 1.43 (t, J=7.2 Hz, 3H).

Example 1B

Preparation of 4-bromo-1-chloro-2-(4-ethoxybenzyl)benzene

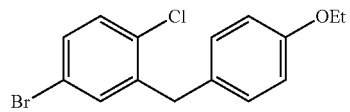 [SMILES: CCOc1ccc(Cc2cc(Br)ccc2Cl)cc1]

To a stirred solution of Example 1A (1.440 kg, 4.26 mol) in anhydrous THF (7.2 L) under nitrogen was added sodium boronhydride (161 g, 4.26 mol) in one portion at 10~15° C. After stirring for 30 min, the mixture was cooled to −5~0° C. and aluminum (III) chloride (1136 g, 8.52 mol) was added carefully portionwise to the reaction mixture over 2 h. The reaction mixture was stirred at 0~5° C. for 3 h after the addition. The reaction mixture was refluxed (65~70° C.) for 15 h. The reaction was concentrated and water (5 kg) was added dropwise slowly in 3~4 h under nitrogen atmosphere so that the internal temperature did not exceed 40° C. The reaction mixture was stirred for 3 h at 0~5° C. The precipitate was filtered and washed with water (1.5 L). The crude product was then dissolved in 7.2 L absolute ethanol at 50~55° C. The solution was slowly cooled to 25° C. in 3 h and at 10~15° C. for 10 h, and 0~5° C. for 2 h. The slurry was filtered and the solid was washed with chilled ethanol (500 mL) and dried under vacuum at 35° C. to afford the crude product. This product was recrystallized from absolute ethanol (5 L) once more and dried under vacuum at 35° C. to give the desired product (1.310 kg, yield 94%; HPLC purity>99%). $^1$H NMR (CDCl$_3$, 400 MHz): δ 7.21~7.29 (m, 3H), 7.11 (d, J=8.8 Hz, 2H,), 6.85 (d, J=8.8 Hz, 2H,), 3.99~4.07 (m, 4H), 1.43 (t, J=7.2 Hz, 3H).

Example 1C

Preparation of (2S,3R,4S,5S,6R)-2-(4-chloro-3-(4-ethoxybenzyl)phenyl)-6-(hydroxymethyl)-2-methoxytetrahydro-2H-pyran-3,4,5-triol

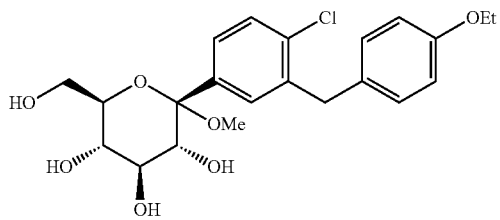 [SMILES: CCOc1ccc(Cc2cc([C@]3(OC)O[C@H](CO)[C@@H](O)[C@H](O)[C@H]3O)ccc2Cl)cc1]

To a solution of Example 1B (200 g, 0.614 mol) in anhydrous toluene/THF (1.2 L, 2:1 (v/v)) was added n-BuLi (2.5 M in hexane, 295 mL) dropwise at −65° C. The reaction was stirred at −65° C. for 30 min. Then the mixture was transferred by a cannula to a solution of (3R,4S,5R,6R)-3,4,5-tris(trimethylsilyloxy)-6-((trimethylsilyloxy)methyl)tetrahydro-2H-pyran-2-one) (373 g, 0.798 mol) in toluene (1.2 L) at −65° C. The mixture was stirred at −65° C. until starting material was consumed (2 h). The reaction was quenched with hydrochloric acid (36~38%, 113 mL, 1.35 mol) in methanol (800 mL), and stirred at room temperature overnight. The reaction was neutralized with saturated sodium bicarbonate to pH 7.5 and the organic phase was separated and the aqueous phase was extracted with ethyl acetate (2×3.0 L). The combined organic layers were washed with brine (2×2.0 L), dried over sodium sulfate and concentrated. The residue was dissolved in hot toluene (600 mL) and poured into n-hexane (2.0 L) with vigorous stirring. After stirring for 1 h, the mixture was filtered and the filter cake was dried under vacuum to give the desired product as a white solid. This solid was used without further purification in the next step. MS ESI (m/z) 439 [M+1]$^+$.

Example 1D

Preparation of (2S,3R,4R,5S,6R)-2-(4-chloro-3-(4-ethoxybenzyl)phenyl)-6-(hydroxymethyl)tetrahydro-2H-pyran-3,4,5-triol, bis(L-proline) complex

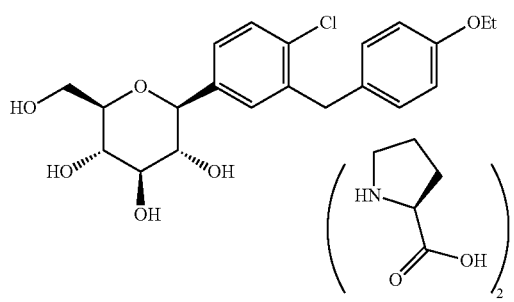

Example 1C (282 g, 0.643 mol) was dissolved in anhydrous acetonitrile/dichloromethane (3.4 L, 1:1 (v/v)) at −45° C. stirred solution of in was added triethylsilane (299 g, 2.57 mol) followed by addition of boron trifluoride etherate (245 mL, 1.93 mol). After the addition, the mixture was stirred for another 2 h at −10° C. The reaction was quenched with saturated aqueous bicarbonate to pH 7.5. The volatiles were removed under reduced pressure and the residues were extracted with ethyl acetate (2×3.0 L). The combined organic layers were washed with brine (2×2.0 L), dried over sodium sulfate and concentrated to give the crude product as a white solid (250 g). Purity (HPLC): 82.8% (UV).

A 5 L 4-necked flask was charged with the above crude product (203 g, 82% purity) and followed by L-proline (114 g, 0.995 mol), ethanol (1.46 L) and water (162 mL). The mixture was heated to reflux for 30 min with rapid mechanical stirring. n-Hexane (200 mL) was added dropwise to the above solution. After the addition was complete, the reaction was cooled slowly to room temperature and then further to −5° C. After stirring for 3 h at −5° C., the mixture was filtered and the filter cake was washed with cold ethanol/water (90:10 (v/v), 2×100 mL) and n-hexane (2×500 mL), and dried under vacuum at 65° C. to give the desired product as a white solid (186 g). A portion of this crude product (140 g) was dissolved in ethanol/water (90:10 (v/v), 700 mL) at 75° C. with mechanical stirring. After the solution became clear, it was cooled slowly to room temperature and stirred for another 5 h. The mixture was filtered and the filter cake was washed with cold ethanol (2×50 mL), n-hexane (2×100 mL), dried under vacuum at 65° C. to get the desired product as a white solid (130 g, yield 66%). Purity (HPLC) 99.5% (UV). $^1$H NMR (CD$_3$OD, 400 MHz): δ 7.34~7.25 (m, 3H), 7.08 (d, J=8.8 Hz, 2H), 6.78 (d, J=8.8 Hz, 2H), 4.10 (d, J=9.2 Hz, 1H), 4.06~3.95 (m, 6H), 3.88~3.85 (m, 1H), 3.72~3.68 (m, 1H), 3.47~3.37 (m, 5H), 3.32~3.20 (m, 3H), 2.33~2.26 (m, 2H), 2.16~2.08 (m, 2H), 2.01~1.95 (m, 4H), 1.35 (t, J=7.2 Hz, 3H); MS ESI (m/z): 409 [M+1]$^+$.

Example 2

Preparation of (2S,3R,4R,5S,6R)-2-(4-chloro-3-(4-ethoxybenzyl)phenyl)-6-(hydroxymethyl)tetrahydro-2H-pyran-3,4,5-triol

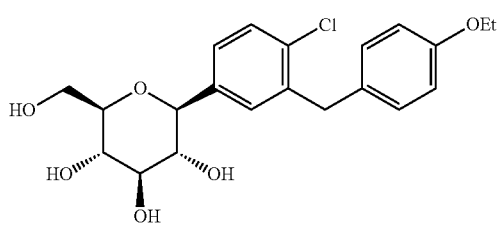 [SMILES: CCOc1ccc(Cc2cc([C@@H]3O[C@H](CO)[C@@H](O)[C@H](O)[C@H]3O)ccc2Cl)cc1]

A suspension of Example 1D (23.0 g, 45.6 mmol) in ethyl acetate (230 mL) and water (230 mL) was heated to 80° C. until the solution became clear. The solution was transferred to a separator funnel immediately. The ethyl acetate layer was separated. Water layer was extracted with ethyl acetate (100 mL). The combined organic layers were washed with brine, dried over sodium sulfate, and concentrated to give the desired product as a white solid (14 g, yield 95%). Purity (HPLC), 99.1% (UV); $^1$H NMR (CD$_3$OD, 400 MHz): δ 7.34~7.25 (m, 3H), 7.08 (d, J=8.8 Hz, 2H), 6.78 (d, J=8.8 Hz, 2H), 4.10 (d, J=9.2 Hz, 1H), 4.06~3.95 (m, 4H), 3.88~3.85 (m, 1H), 3.69~3.65 (m, 1H), 3.47~3.37 (m, 3H), 3.27 (m, 1H), 1.35 (t, J=7.2 Hz, 3H); MS ESI (m/z): 409 [M+1]$^+$.

Example 3

Preparation of (2S,3R,4R,5S,6R)-2-(4-chloro-3-(4-methoxybenzyl)phenyl)-6-(hydroxymethyl)tetrahydro-2H-pyran-3,4,5-triol, bis(L-proline) complex (3B)

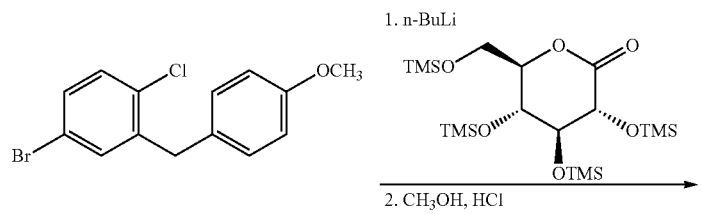

-continued

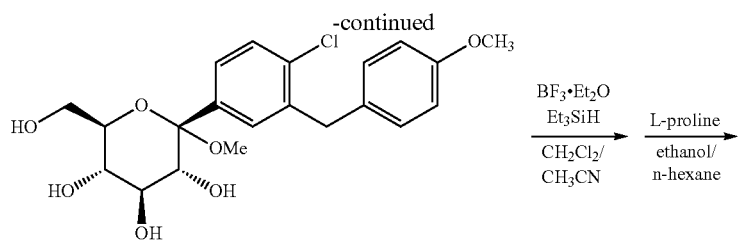

Example 3A

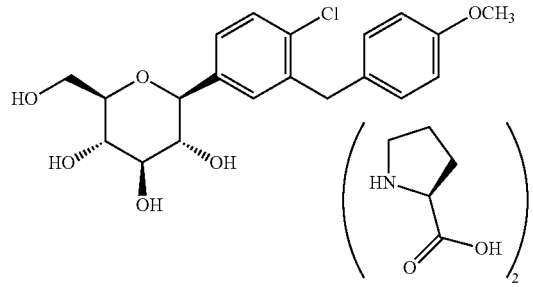

Example 3B

Example 3A

Preparation of (2S,3R,4S,5S,6R)-2-(4-chloro-3-(4-methoxybenzyl)phenyl)-6-(hydroxymethyl)-2-methoxytetrahydro-2H-pyran-3,4,5-triol

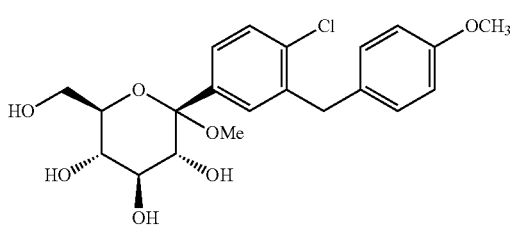 [SMILES: COc1ccc(Cc2cc([C@]3(OC)O[C@H](CO)[C@@H](O)[C@H](O)[C@H]3O)ccc2Cl)cc1]

A cold (−78° C.) solution of n-BuLi (124 mL, 2.5 M in hexane, 0.310 mol) was added dropwise under argon to a solution of 4-bromo-1-chloro-2-(4-methoxybenzyl)benzene (80 g, 0.258 mol) in dry THF/toluene (1:2 (v/v), 480 mL) cooled at −78° C. at such a rate as to keep the reaction temperature below −70° C. After the addition, the mixture was stirred for 40 min before transferred by a cannula to a stirred solution of (3R,4S,5R,6R)-3,4,5-tris(trimethylsilyloxy)-6-((trimethylsilyloxy)methyl)tetrahydro-2H-pyran-2-one (157 g, 0.335 mol) in toluene (480 mL) precooled to −78° C. at a rate as to keep the internal temperature below −70° C. The mixture was stirred for 3 h at −78° C. until starting material was consumed and was quenched slowly by hydrochloric acid (36-38%, 47.3 mL, 0.567 mol) in methanol (320 mL), keeping the internal temperature below −45° C. The reaction mixture was gradually warmed to room temperature and stirred overnight. The mixture was neutralized with saturated sodium bicarbonate aqueous solution to pH 7.5. The organic layer was separated and the aqueous phase was extracted with ethyl acetate (2×1.0 L). The combined organic layers were washed with brine (2×1.0 L), dried over sodium sulfate, and concentrated. The residue was dried under vacuum at 40° C. to give the crude product as an off-white solid (111 g), which was used in the next step without further purification. Purity (HPLC) 66% (UV); MS ESI (m/z) 425 [M+1]$^+$.

Example 3B

Preparation of (2S,3R,4R,5S,6R)-2-(4-chloro-3-(4-methoxybenzyl)phenyl)-6-(hydroxymethyl)tetrahydro-2H-pyran-3,4,5-triol, bis(L-proline) complex

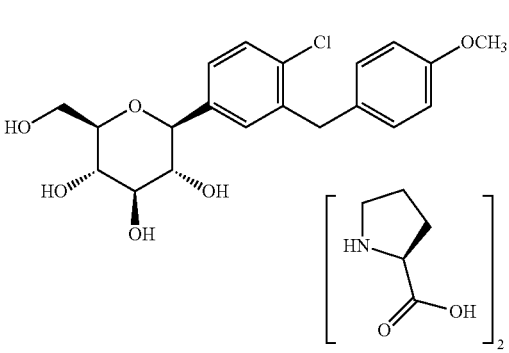

To a stirred solution of Example 3A (111 g, 0.262 mol) in anhydrous acetonitrile/dichloromethane (1:1 (v/v), 1.32 L) was added triethylsilane (122 g, 1.05 mol) at −45° C. and followed by boron trifluoride etherate (100 mL, 0.785 mol). The mixture was stirred at −10° C. for 2 h. The reaction was quenched with aqueous solution of saturated bicarbonate to pH 7.5. The volatiles were removed under reduced pressure and the residue was extracted with ethyl acetate (2×1.0 L). The combined organic layers were washed with brine (2×1.0 L), dried over sodium sulfate, and concentrated to give the crude product as a white solid (110 g). Purity (LC-MS) 2.6 min, 76.5% (UV).

A suspension of the above crude product (110 g, purity 76.5%) and L-proline (64.2 g, 0.558 mole) in ethanol (836 mL) and water (44 mL) in a 5 L 4-necked flask was refluxed for 30 min with rapid mechanical stirring, to which n-Hexane (1.2 L) was added dropwise. After the addition, the solution was cooled slowly to room temperature and then cooled to 5° C. After stirring for 3 h at 5° C., the mixture was filtered and the filter cake was washed with n-hexane (2×300 mL), dried under vacuum at 65° C. to give the complex as a white solid (110 g). The crude product was recrystallized again in 95% ethanol (330 mL) by the same procedure as described in Example 1 to give the desired product (75 g, yield 52.5%). Purity (HPLC) 99.5% (UV); $^1$H NMR (CD$_3$OD, 400 MHz): δ 7.34~7.25 (m, 3H), 7.08 (d, J=8.4 Hz, 2H), 6.79 (d, J=8.4 Hz, 2H), 4.10 (d, J=9.6 Hz, 1H), 4.05~3.97 (m, 4H), 3.88 (d, J=11.2 Hz, 1H), 3.76 (s, 3H), 3.73~3.69 (m, 1H), 3.49~3.37 (m, 5H), 3.32~3.21 (m, 3H), 2.36~2.27 (m, 2H), 2.17~2.08 (m, 2H), 2.01~1.95 (m, 4H); MS ESI (m/z): 395 [M+1]$^+$.

Example 4

Preparation of (2S,3R,4R,5S,6R)-2-(4-chloro-3-(4-cyclopropylbenzyl)phenyl)-6-(hydroxymethyl)tetrahydro-2H-pyran-3,4,5-triol, bis(L-proline) complex

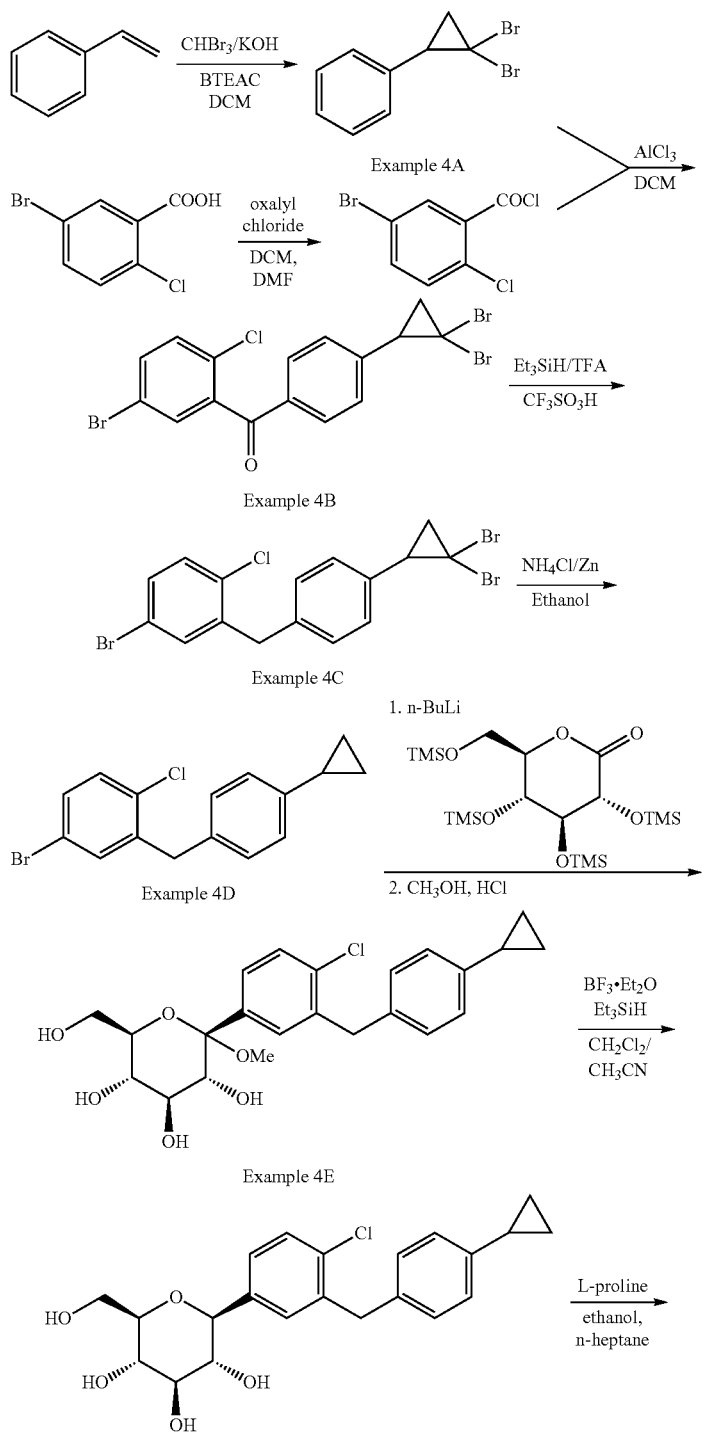

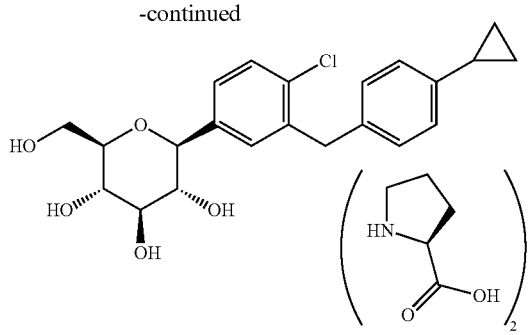

Example 4F

Example 4A

Preparation of (2,2-dibromocyclopropyl)benzene

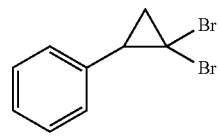 [SMILES: BrC1(Br)CC1c1ccccc1]

In a 1 liter 3-neck flask, bromoform (312 g, 1.23 mol) was added dropwise over 120 min to stirred solution of styrene (100 g, 0.96 mol), benzyltriethylammonium chloride (7 g, 0.031 mol) and powdered potassium hydroxide (80.6 g, 1.44 mol) in dichloromethane (480 mL) at 40° C. The mixture was stirred at 25° C. for 20 h. The reaction mixture was filtered through a short plug of silica and the filtrate was concentrated. The dark residue was distilled at 80° C. under reduced pressure (about 50 Pa) to give the desired product as pale yellow liquid (233 g, yield 88%, purity 98% by HPLC (UV)). $^1$H NMR (CDCl$_3$, 400 MHz): δ 7.38~7.42 (m, 3H), 7.29~7.31 (m, 2H), 2.98~3.03 (m, 1H), 2.15~2.20 (m, 1H), 2.04~2.08 (m, 1H).

Example 4B

Preparation of (5-bromo-2-chlorophenyl)(4-(2,2-dibromocyclopropyl)phenyl)methanone

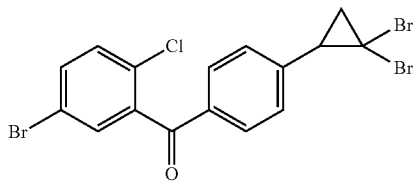 [SMILES: O=C(c1ccc(C2CC2(Br)Br)cc1)c1cc(Br)ccc1Cl]

DMF (0.5 mL) was added to a stirred solution of 5-bromo-2-chlorobenzoic acid (60 g, 0.255 mol) and oxalyl chloride (38.7 g, 0.305 mol) in dichloromethane (240 mL) at room temperature. The mixture was stirred at room temperature for 20 h before being concentrated to a light yellow oil. To the mixture of this oil and Example 4A (63 g, 0.228 mol) in dichloromethane (300 mL) cooled to 0° C. was added aluminum trichloride (43.2 g, 0.324 mol) in portions over ~1 h. The reaction mixture was allowed to warm to room temperature and stirred for 3 h. Water (150 mL) was added to quenched the reaction. The organic phase was separated and the water phase was extracted with ethyl acetate (600 mL). The combined organic phases were washed with water (2×300 mL), brine (300 mL), dried over anhydrous Na$_2$SO$_4$ and concentrated to give the desired product as yellow oil (104 g, yield 92.9%), which was used directly in the next step. $^1$H NMR (CDCl$_3$, 400 MHz): δ 7.70~7.95 (m, 2H), 7.45~7.53 (m, 2H), 7.19~7.37 (m, 3H), 2.98~3.03 (m, 1H), 2.15~2.20 (m, 1H), 2.04~2.08 (m, 1H).

Example 4C

Preparation of 4-bromo-1-chloro-2-(4-(2,2-dibromocyclopropyl)benzyl)benzene

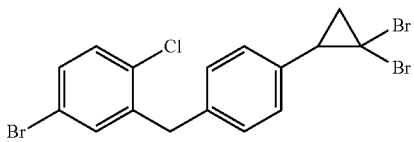 [SMILES: Clc1ccc(Br)cc1Cc1ccc(C2CC2(Br)Br)cc1]

Trifluoromethanesulfonic acid (0.5 g, 0.0033 mol) was added slowly to a stirred solution of Example 4B (104 g, 0.211 mol) and triethylsilane (66.8 g, 0.574 mol) in trifluoroacetic acid (300 mL) cooled to 30° C. in a water-bath. The reaction became refluxed. After 0.5 h, the water bath was replaced by an oil bath. The reaction mixture was heated to reflux for 3 h. After cooling to room temperature, the reaction mixture was allowed to stir for another 1 h. The solid was filtered, washed with hexane (100 mL) and dried under vacuum at 30° C. to get the desired product as a pale gray solid (86.4 g, yield 85%) $^1$H NMR (CDCl$_3$, 400 MHz): δ 7.28~7.34

(m, 3H), 7.18~7.25 (m, 4H), 4.08 (s, 1H), 2.93~2.98 (m, 1H), 2.13~2.17 (m, 1H), 2.00~2.03 (m, 1H).

Example 4D

Preparation of 4-bromo-1-chloro-2-(4-cyclopropylbenzyl)benzene

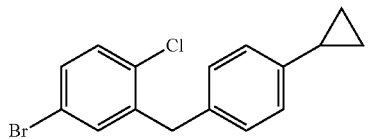 [SMILES: Clc1ccc(Br)cc1Cc1ccc(C2CC2)cc1]

Zinc dust (4.8 g, 0.073 mol) and ammonium chloride (5.3 g, 0.1 mol) were added to a stirred solution of Example 4C (4.79 g, 0.01 mol) in ethanol (20 mL). The mixture was heated to 70° C. for 20 h. The reaction mixture was filtered, the solid was washed with ethyl acetate (30 mL). The filtrate was concentrated to give light yellow oil. The residue was dissolved in ethyl acetate (30 mL), which was washed with water (15 mL), brine (15 mL) and concentrated to give a light yellow oil (3.0 g). The oil in methanol (50 mL) and hexane (5 mL) was heated to reflux for 1 h. The mixture was cooled to −30° C. and the precipitates were filtered and the solid was dried under reduced pressure to give the desired product as a white solid (1.2 g, yield 32.5%, purity 92.0% by LC-MS). $^1$H NMR (400 MHz, CDCl$_3$) δ 7.47~7.44 (m, 1H), 7.24~7.21 (m, 2H), 7.18 (d, J=8.4 Hz, 2H), 7.09 (d, J=8.4 Hz, 2H), 4.15 (s, 2H), 1.99~1.92 (m, 1H), 1.04~1.00 (m, 2H), 0.78~0.74 (m, 2H).

Example 4E

Preparation of (3R,4S,5S,6R)-2-(4-chloro-3-(4-cyclopropylbenzyl)phenyl)-6-(hydroxymethyl)-2-methoxytetrahydro-2H-pyran-3,4,5-triol

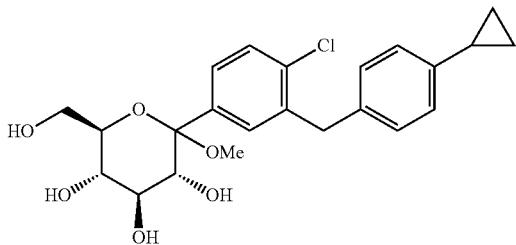 [SMILES: COC1(c2ccc(Cl)c(Cc3ccc(C4CC4)cc3)c2)O[C@H](CO)[C@@H](O)[C@H](O)[C@H]1O]

A cold solution of n-BuLi (2.5 M in hexane, 163 mL, 0.408 mol) precooled to −78° C. can be added dropwise under argon to a stirred solution of 4-bromo-1-chloro-2-((4-cyclopropylphenyl)methyl)benzene (100 g, 0.340 mol) in anhydrous THF/toluene (1:2 (v/v), 660 mL) at −78° C. at such a rate as to keep the internal temperature below −70° C. The mixture is then stirred for another 40 min after the addition. The reaction mixture is transferred by a cannula to a stirred solution of (3R,4S,5R,6R)-3,4,5-tris-(trimethylsilyloxy)-6-((trimethylsilyloxy)methyl)-tetrahydropyran-2-one (206 g, 0.442 mol) in toluene (660 mL) at −78° C. at a rate as to keep the internal temperature below −70° C. The reaction mixture is then stirred at −78° C. for 3 h until the starting materials are consumed before quenching slowly with a solution of hydrochloric acid (36~38%, 62.3 mL, 0.747 mol) in methanol (440 mL), so the reaction temperature does not exceed −45° C. The reaction mixture is gradually warmed to room temperature and stirred overnight. The mixture is neutralized with aqueous solution of saturated sodium bicarbonate to pH 7.5. The organic layer is separated and the aqueous phase is extracted with ethyl acetate (2×1.2 L). The combined organic layers can be washed with brine (2×1.0 L), dried over sodium sulfate, and concentrated. The residue is then dissolved in hot toluene (200 mL), to which n-hexane (2.0 L) is poured in with rapid stirring. The mixture is stirred for another 1 h and filtered. The solid is dried under vacuum to give the crude product, which can be used in the next step without further purification.

Example 4F

Preparation of (2S,3R,4R,5S,6R)-2-(4-chloro-3-(4-cyclopropylbenzyl)phenyl)-6-(hydroxymethyl)tetrahydro-2H-pyran-3,4,5-triol, bis(L-proline) complex

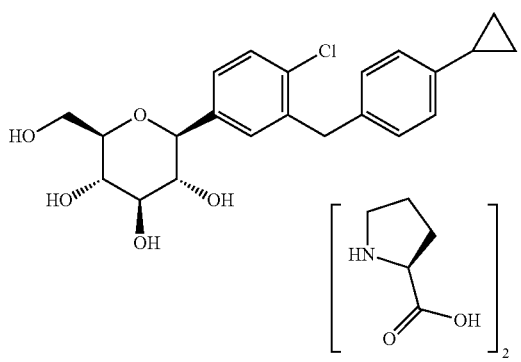

To a stirred solution of Example 4A (118 g, 0.270 mol) in anhydrous acetonitrile/dichloromethane (1:1 (v/v), 1.42 L) is added triethylsilane (126 g, 1.08 mol) at −45° C., followed by boron trifluoride etherate (103 mL, 0.812 mol). The mixture is stirred at −10° C. for 2 h before quenching with aqueous solution of saturated bicarbonate to pH 7.5. The volatiles are removed under reduced pressure and the residue is extracted with ethyl acetate (2×1.5 L). The combined organic layers are washed with brine (2×1.0 L), dried over sodium sulfate, and concentrated to give the crude product as a white solid. A suspension of the above crude product (105 g) and L-proline (59.5 g, 0.517 mole) in ethanol (798 mL) and water (42 mL) in a 5 L four-necked flask is refluxed for 30 min with rapid mechanical stirring. n-Heptane (1.05 L) is added dropwise to the above hot solution. After the addition, the mixture is cooled slowly to room temperature and stirred for another 5 h. The reaction mixture is then filtered and the filter cake is washed with n-heptane (2×300 mL), and dried under vacuum at 55° C. to give the crude complex as a white solid. This sample is stirred in 95% ethanol (354 mL) and heated to 75° C. until a clear solution is formed, to which n-heptane (590 mL) is added dropwise. The mixture is cooled slowly to room temperature and stirring is continued for another 5 h. The reaction mixture is filtered and the filter cake is washed with n-heptane (2×200 mL), and dried under vacuum at 65° C. to give the complex as a white solid (105 g). This solid can be recrystallized in 95% ethanol by the same procedure as described in Example 1 to give the pure desired product.

Example 5
Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex (5F)
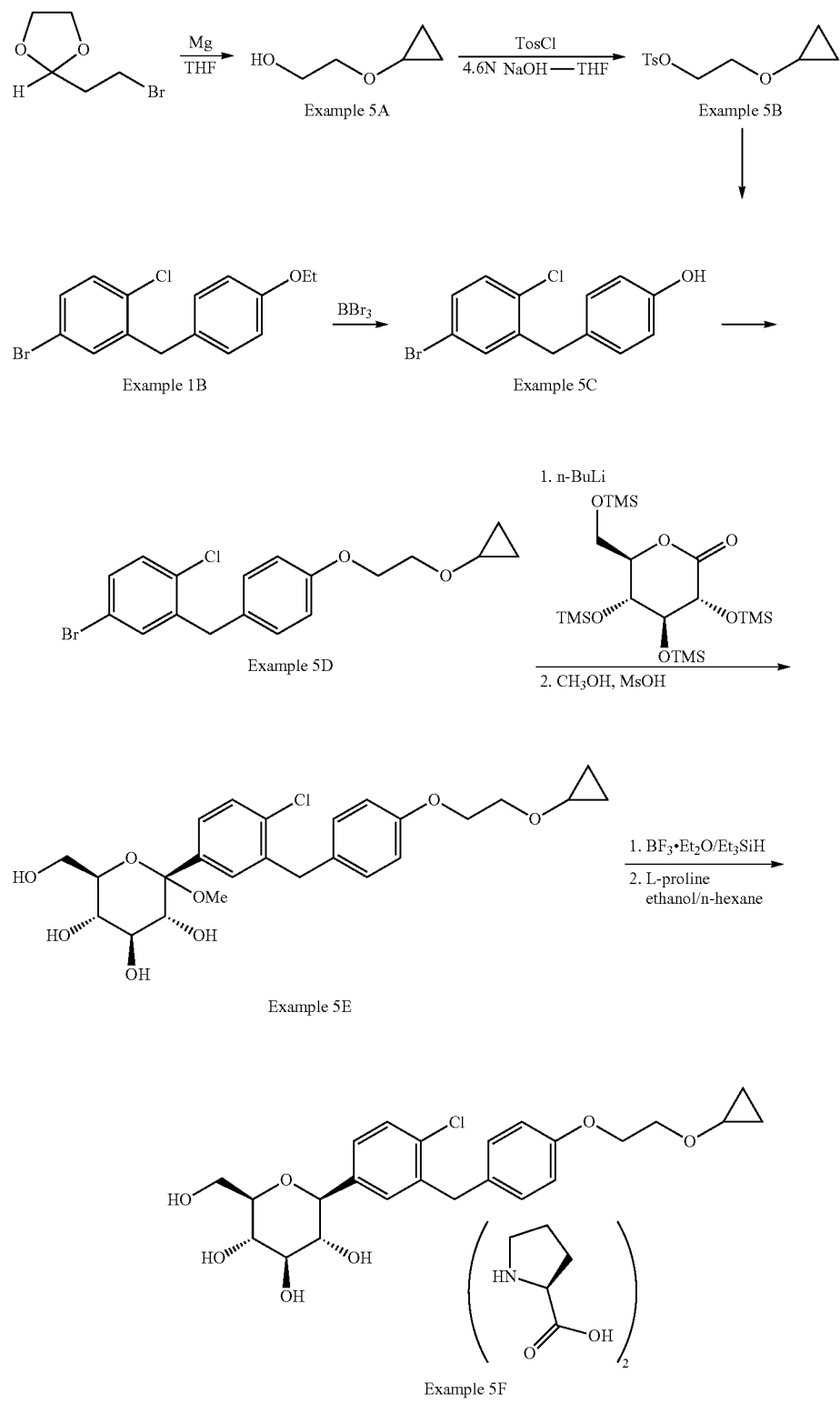

Example 5A

Preparation of 2-cyclopropoxyethanol

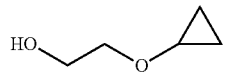

To a suspension of Mg powder (86.7 g, 3.6 mol) and iodine (cat) in anhydrous THF (0.7 L) was added slowly 1,2-dibromoethane (460 g, 2.4 mol) in anhydrous THF (2 L) slowly at a rate as to keep the internal temperature between 40-55° C. After the addition, a solution of 2-(2-bromoethyl)-1,3-dioxolane (100 g, 0.56 mol) in anhydrous THF (750 mL) was added dropwise. The reaction mixture was kept at 40-55° C. for 16 h and was quenched by addition of aqueous solution of ammonium chloride. The mixture was extracted with methylene chloride. The organic layer was dried over sodium sulfate, and concentrated to give the title product (27 g) as yellow oil, which was directly used without further purification.

Example 5B

Preparation of 2-cyclopropoxyethyl 4-methylbenzenesulfonate

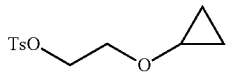

To a stirred solution of sodium hydroxide (32 g, 0.8 mol) in water (180 mL) and THF (180 mL) was added Example 5A (27 g, 0.26 mol) at −5 to 0° C. Afterwards, a solution of p-toluenesulfonyl chloride (52 g, 0.27 mol) in THF (360 mL) was added dropwise. The reaction mixture was kept at −5 to 0° C. for 16 h. The reaction mixture was then kept at room temperature for 30 min. The organic layer was separated and the aqueous layer was extracted with ethyl acetate (2×1.0 L). The combined organic layers were washed with brine, dried over $Na_2SO_4$ and concentrated to get the crude product as yellow oil (53.3 g). It was used directly without further purification.

Example 5C

Preparation of 4-(5-bromo-2-chlorobenzyl)phenol

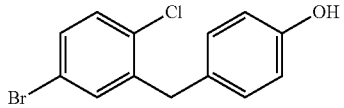 [SMILES: Oc1ccc(Cc2cc(Br)ccc2Cl)cc1]

To a stirred solution of Example 1B (747 g, 2.31 mol) in dichloromethane was added boron tribromide (1.15 kg, 4.62 mol) slowly at −78° C. The reaction mixture was allowed to rise to room temperature. When the reaction was complete as measure by TLC, the reaction was quenched with water. The mixture was extracted with dichloromethane. The organic layer was washed with aqueous solution of saturated sodium bicarbonate, water, brine, dried over $Na_2SO_4$, and concentrated. The residue was recrystallized in petroleum ether to give the title compound as a white solid (460 g, yield 68%). $^1$H NMR (CDCl$_3$, 400 MHz): δ 7.23~7.29 (m, 3H), 7.08 (d, J=8.8 Hz, 2H), 6.79 (d, J=8.8 Hz, 2H), 5.01 (s, 1H), 4.00 (s, 2H).

Example 5D

Preparation of 4-bromo-1-chloro-2-(4-(2-cyclopropoxyethoxy)benzyl)benzene

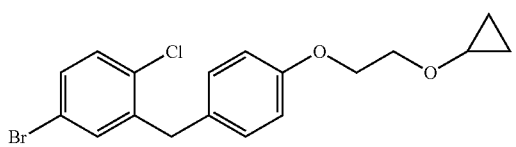 [SMILES: Clc1ccc(Br)cc1Cc1ccc(OCCOC2CC2)cc1]

A mixture of Example 5C (56.7 g, 210 mmol) and $Cs_2CO_3$ (135 g, 420 mmol) in DMF (350 mL) was stirred at room temperature for 0.5 h. Example 5B (53.3 g, 210 mmol) was added. The reaction mixture was stirred at room temperature overnight. It was diluted with water (3 L) and extracted with EtOAc. The organic layer was washed with water, brine, dried over $Na_2SO_4$, and concentrated. The residue was purified by flash column chromatography on silica gel eluting with petroleum ether:ethyl acetate (10:1) to give the title compound as liquid (51 g, yield 64%). $^1$H NMR (CDCl$_3$, 400 MHz): δ 7.22~7.29 (m, 3H), 7.08 (d, J=8.8 Hz, 2H), 6.88 (d, J=8.8 Hz, 2H), 4.10 (t, J=4.8 Hz, 2H), 3.86 (t, J=4.8 Hz, 2H), 3.38-3.32 (m, 1H), 0.62-0.66 (m, 2H), 0.49-0.52 (m, 2H).

Example 5E

Preparation of (2S,3R,4S,5S,6R)-2-(4-chloro-3-(4-(2-cyclopropoxyethoxy)benzyl)phenyl)-6-(hydroxymethyl)-2-methoxytetrahydro-2H-pyran-3,4,5-triol

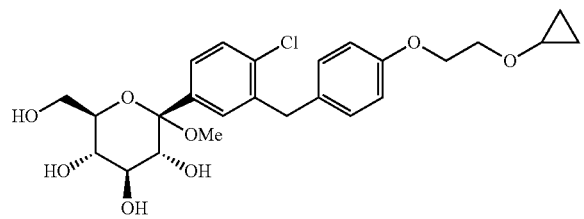 [SMILES: CO[C@@]1(c2ccc(Cl)c(Cc3ccc(OCCOC4CC4)cc3)c2)O[C@H](CO)[C@@H](O)[C@H](O)[C@H]1O]

To a stirred solution of Example 5D (213 g) in anhydrous THF/toluene (1:2 (v/v), 1.7 L) under argon was added n-BuLi (2.5 M hexane, 245.9 mL) drop wise at −60±5° C. The mixture was stirred for 30 min. before transferred to a stirred solution of 2,3,4,6-tetra-O-trimethylsilyl-β-D-glucolactone (310.5 g) in toluene (1.6 L) at −60±5° C. The reaction mixture was continuously stirred at −60±5° C. for 1 h before quenching with aqueous solution of saturated ammonium chloride (1.5 L). Then mixture was allowed to warm to room temperature and stirred for 1 h. The organic layer was separated and the water layer was extracted with ethyl acetate (3×500 mL). The combined organic layers were washed with brine (1 L), dried over Na₂SO₄, and concentrated. The residue was dissolved in methanol (450 mL) and methanesulfonic acid (9.2 mL) was added at 0° C. The solution was allowed to warm to room temperature and stirred for 20 h. It was quenched with aqueous solution of sodium bicarbonate (50 g) in water (500 mL) and additional water (900 mL) was added. The mixture was extracted with ethyl acetate (3×1.0 L). The combined organic layers were washed with brine, dried over Na₂SO₄, concentrated and used directly in the next step without further purification.

Example 5F

Preparation of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex

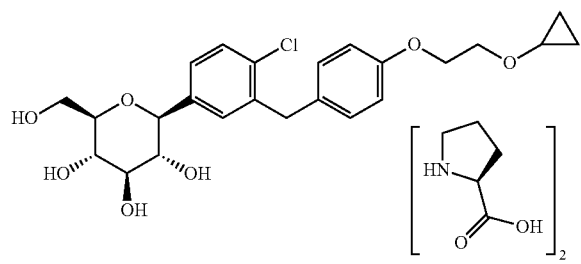

To stirred solution of Example 5E in CH₂Cl₂/CH₃CN (650 mL:650 mL) at −5° C. was added triethylsilane (28.2 mL, 563 mmol), and followed by BF₃.Et₂O (52.3 mL, 418.9 mmol). The reaction was stirred for 16 h while the temperature was allowed to warm to room temperature gradually. The reaction was quenched with aqueous solution of saturated sodium bicarbonate to pH 8.0. The organic volatiles were removed under vacuum. The residue was partitioned between ethyl acetate (2.25 L) and water (2.25 L). The organic layer was separated, washed with brine, dried over Na₂SO₄ and concentrated to give the crude product (230 g, purity 82.3%). This product and L-proline (113.7 g) in EtOH/H₂O (15:1 v/v, 2.09 L) was stirred at 80° C. for 1 h when it became a clear solution. Hexane (3.0 L) was added dropwise into the above hot solution over 50 min, with the temperature being kept at about 60° C. The reaction mixture was stirred overnight at room temperature. The solid was filtered and washed with EtOH/H₂O (15:1 (v/v), 2×300 mL), hexane (2×900 mL), and dried at 45° C. under vacuum for 10 h to give the pure title compound as a white solid (209 g). Purity (HPLC) 99.2% (UV). ¹H NMR (CD₃OD, 400 MHz): δ 7.25~7.34 (m, 3H), 7.11 (d, J=8.8 Hz, 2H), 6.84 (d, J=8.8 Hz, 2H), 4.03-4.11 (m, 5H), 3.96-4.00 (m, 2H), 3.83-3.90 (m, 3H), 3.68-3.72 (m, 1H), 3.36-3.46 (m, 6H), 3.21-3.30 (m, 3H), 2.26-2.34 (m, 2H), 2.08-2.17 (m, 2H), 1.94-2.02 (m, 4H), 0.56-0.57 (m, 2H), 0.52-0.53 (m, 2H).

Example 6

(2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol

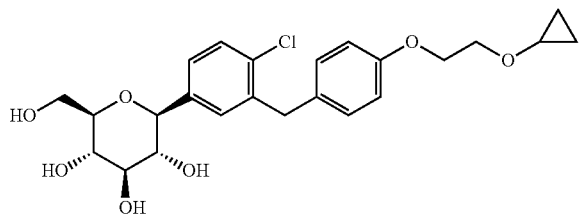

Example 5F (40 g, purity 99.8%) in water (400 mL) was stirred and heated to 60° C. for 1 h. Ethyl acetate (1.0 L) was added dropwise at 60° C. over 1 h. The mixture was stirred for another 1 h. After cooling, the organic layer was separated, washed with water (3×), dried over Na₂SO₄ and concentrated to give the title compound as a glassy solid (24.0 g, purity 99.8%). ¹H NMR (CD₃OD, 400 MHz): δ 7.25-7.34 (m, 3H), 7.11 (d, J=8.8 Hz, 2H), 6.84 (d, J=8.8 Hz, 2H), 4.03-4.11 (m, 5H), 3.83-3.90 (m, 3H), 3.68-3.72 (m, 1H), 3.36~3.46 (m, 4H), 3.21-3.30 (m, 3H), 0.56-0.57 (m, 2H), 0.52-0.53 (m, 2H).

Example 7

Figure 2:
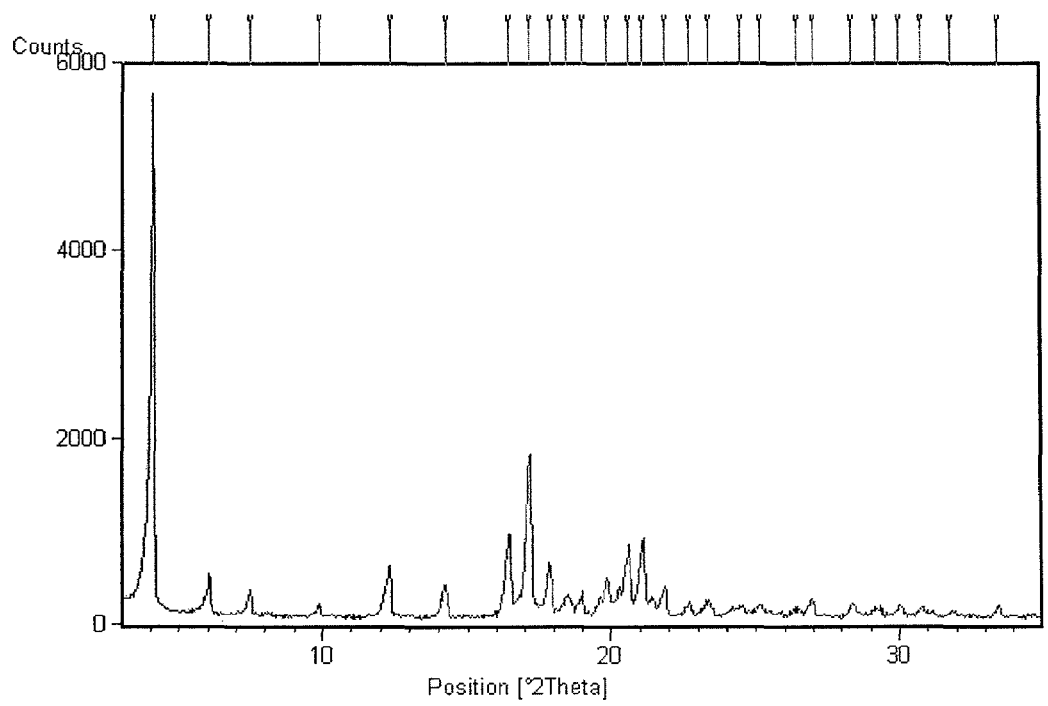
FIG. 2 is the X-ray powder diffraction pattern for the complex of Example 5F of the invention.
Figure 3:
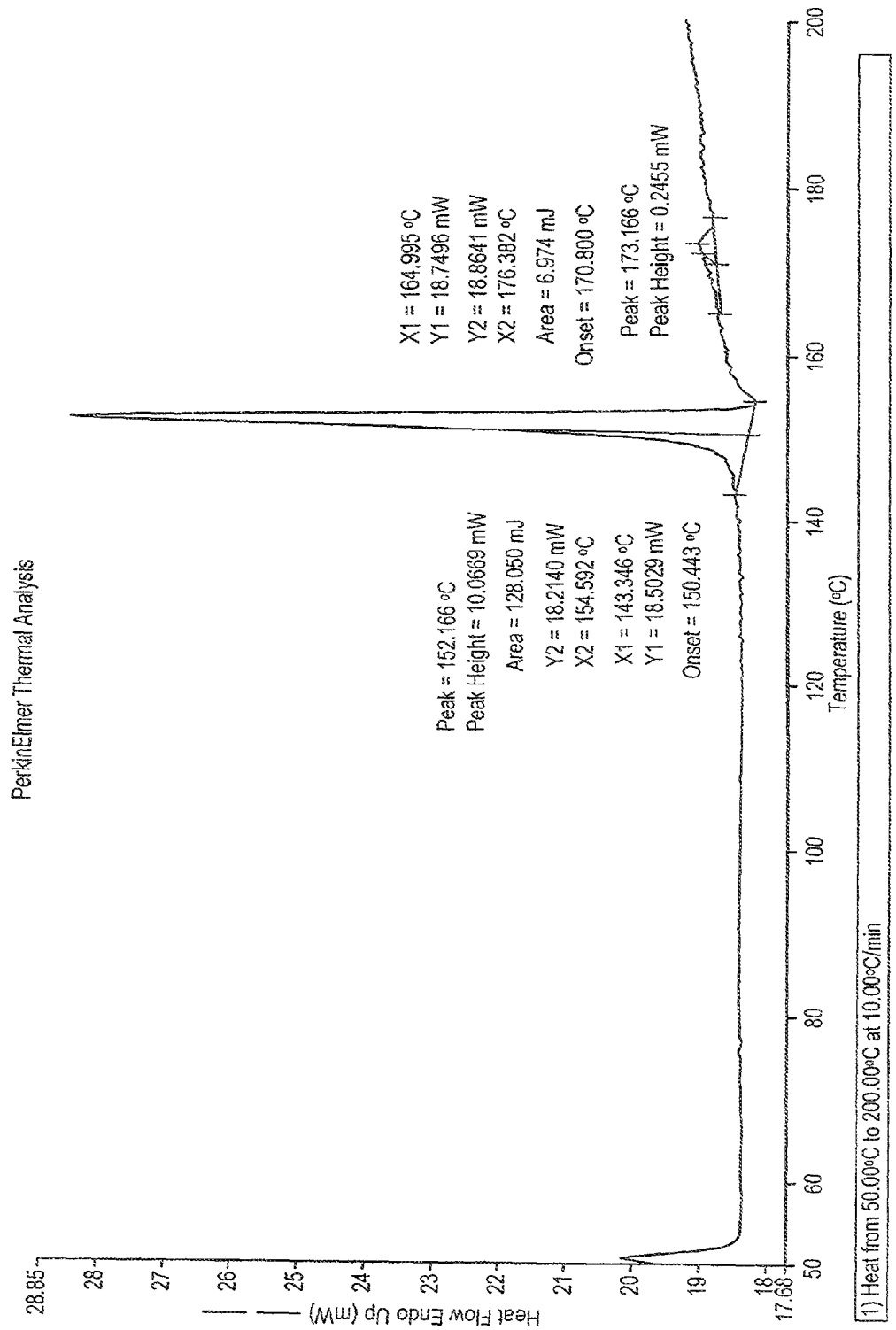
FIG. 3 is the differential scanning calorimetry spectrum for the complex of Example 6 of the invention.

Crystalline complex of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex (see Example 5F) was analyzed by X-ray powder diffraction using CuK$_{α1}$ radiation. The diffraction pattern is shown in FIG. 2 and summarized in Table 1 (only peaks up to 30° in 2θ are listed). The melting point of the complex was determined by differential scanning calorimetry (DSC) as 151±1° C. (evaluated as onset-temperature; heating from 50° C. to 200° C. at 10° C./min). The DSC spectrum is shown in FIG. 3.

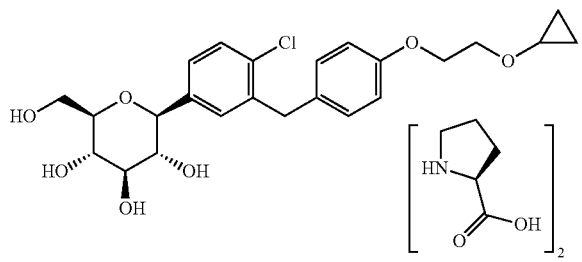

TABLE 1

| Position [°2θ] | d-spacing [Å] | Relative Intensity [%] |
|---|---|---|
| 4.08 | 21.62 | 100.0 |
| 6.04 | 14.63 | 8.1 |

TABLE 1-continued

| Position [°2θ] | d-spacing [Å] | Relative Intensity[%] |
|---|---|---|
| 7.50 | 11.77 | 5.3 |
| 9.88 | 8.95 | 2.3 |
| 12.31 | 7.18 | 9.9 |
| 14.22 | 6.22 | 6.7 |
| 16.44 | 5.39 | 16.3 |
| 17.18 | 5.16 | 30.9 |
| 17.89 | 4.96 | 9.6 |
| 18.47 | 4.80 | 4.1 |
| 18.97 | 4.67 | 4.0 |
| 19.85 | 4.47 | 7.7 |
| 20.60 | 4.31 | 14.1 |
| 21.10 | 4.21 | 14.8 |
| 21.88 | 4.06 | 5.9 |
| 22.72 | 3.91 | 2.7 |
| 23.38 | 3.80 | 2.8 |
| 24.49 | 3.63 | 2.1 |
| 25.17 | 3.54 | 2.5 |
| 26.43 | 3.37 | 1.4 |
| 26.97 | 3.30 | 3.1 |
| 28.36 | 3.14 | 2.2 |
| 29.23 | 3.05 | 1.6 |

What is claimed is:

1. A crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex characterized by an X-ray powder diffraction pattern that comprises peaks at 4.08, 17.19 and 21.12 degrees 2θ (±0.05 degrees 2θ), wherein said X-ray powder diffraction pattern is made using CuK$_{α1}$ radiation.

2. A crystalline form in accordance with claim 1, characterized by an X-ray powder diffraction pattern that comprises peaks at 4.08, 6.04, 17.19, 19.86 and 21.12 degrees 2θ (±0.05 degrees 2θ).

3. A crystalline form in accordance with claim 1, characterized by an X-ray powder diffraction pattern that comprises peaks at 4.08, 6.04, 14.23, 16.45, 17.19, 17.89, 19.86, 20.61 and 21.12 degrees 2θ (+0.05 degrees 2θ).

4. A crystalline form in accordance with claim 1, characterized by an X-ray powder diffraction pattern that comprises peaks at 4.08, 6.04, 7.50, 9.88, 12.31, 14.23, 16.45, 17.19, 17.89, 18.47, 18.97, 19.86, 20.61 and 21.12 degrees 2θ (±0.05 degrees 2θ).

5. A crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex characterized by a melting point of about 151° C.±1° C., as determined by differential scanning calorimetry with heating from 50° C. to 200° C. at a rate of 10° C./min.

6. A crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex characterized by an X-ray powder diffraction pattern with peaks and relative intensities (%) as follows: 4.08, (100); 6.04, (8.1); 7.50, (5.3); 9.88, (2.3); 12.31, (9.9); 14.22, (6.7); 16.44, (16.3); 17.18, (30.9); 17.89, (9.6); 18.47, (4.1); 18.97, (4.0); 19.85, (7.7); 20.60, (14.1); 21.10, (14.8); 21.88, (5.9); 22.72, (2.7); 23.38, (2.8); 24.49, (2.1); 25.17, (2.5); 26.43, (1.4); 26.97, (3.1); 28.36, (2.2); and 29.23 (1.6) degrees 2θ (±0.05 degrees 2θ).

7. A crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, bis(L-proline) complex characterized by an X-ray powder diffraction pattern that comprises peaks at 4.08, 6.04, 7.50, 9.88, 12.31, 14.22, 16.44, 17.18, 17.89, 18.47, 18.97, 19.85, 20.60, 21.10, 21.88, 22.72, 23.38, 24.49, 25.17, 26.43, 26.97, 28.36 and 29.23 degrees 2θ (±0.05 degrees 2θ).

* * * * *